US012121726B2

(12) United States Patent
Levine et al.

(10) Patent No.: US 12,121,726 B2
(45) Date of Patent: Oct. 22, 2024

(54) CONTROL OF VAGAL STIMULATION

(71) Applicant: SetPoint Medical Corporation, Valencia, CA (US)

(72) Inventors: Jacob A. Levine, West Hempstead, NY (US); Michael A. Faltys, Valencia, CA (US); Jesse M. Simon, Los Angeles, CA (US)

(73) Assignee: SetPoint Medical Corporation, Valencia, CA (US)

( * ) Notice: Subject to any disclaimer, the term of this patent is extended or adjusted under 35 U.S.C. 154(b) by 0 days.

(21) Appl. No.: 18/151,407

(22) Filed: Jan. 6, 2023

(65) Prior Publication Data

US 2023/0158301 A1   May 25, 2023

Related U.S. Application Data

(63) Continuation of application No. 16/916,036, filed on Jun. 29, 2020, now Pat. No. 11,547,852, which is a
(Continued)

(51) Int. Cl.
| | |
|---|---|
| *A61B 5/352* | (2021.01) |
| *A61B 5/00* | (2006.01) |
| *A61B 5/024* | (2006.01) |
| *A61N 1/36* | (2006.01) |
| *A61N 1/372* | (2006.01) |
| *A61N 1/375* | (2006.01) |

(Continued)

(52) U.S. Cl.
CPC ........ *A61N 1/3606* (2013.01); *A61B 5/02405* (2013.01); *A61B 5/352* (2021.01); *A61B 5/4035* (2013.01); *A61B 5/4836* (2013.01); *A61B 5/7257* (2013.01); *A61N 1/36053* (2013.01); *A61N 1/36135* (2013.01); *A61N 1/37205* (2013.01); *A61N 1/3756* (2013.01); *A61N 1/0556* (2013.01); *A61N 1/37247* (2013.01); *A61N 1/3787* (2013.01)

(58) Field of Classification Search
CPC .............................. A61N 1/3606; A61B 5/352
USPC ......................................................... 607/62
See application file for complete search history.

(56) References Cited

U.S. PATENT DOCUMENTS

| | | | |
|---|---|---|---|
| 2,164,121 | A | 6/1939 | Pescador |
| 3,363,623 | A | 1/1968 | Atwell |

(Continued)

FOREIGN PATENT DOCUMENTS

| | | | |
|---|---|---|---|
| CN | 201230913 A | 5/2009 | |
| CN | 101528303 A | 9/2009 | |

(Continued)

OTHER PUBLICATIONS

US 6,184,239 B1, 02/2001, Puskas (withdrawn)
(Continued)

*Primary Examiner* — Nadia A Mahmood
(74) *Attorney, Agent, or Firm* — Shay Glenn LLP

(57) ABSTRACT

Methods and apparatuses for stimulation of the vagus nerve to treat inflammation including adjusting the stimulation based on one or more metric sensitive to patient response. The one or more metrics may include heart rate variability, level of T regulatory cells, particularly memory T regulatory cells, temperature, etc. Stimulation may be provided through an implantable microstimulator.

23 Claims, 23 Drawing Sheets

Related U.S. Application Data continuation of application No. 15/411,933, filed on Jan. 20, 2017, now Pat. No. 10,695,569.

(60) Provisional application No. 62/340,950, filed on May 24, 2016, provisional application No. 62/286,950, filed on Jan. 25, 2016, provisional application No. 62/286,957, filed on Jan. 25, 2016, provisional application No. 62/281,135, filed on Jan. 20, 2016.

(51) Int. Cl.
  *A61N 1/05* (2006.01)
  *A61N 1/378* (2006.01)

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Lasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |

(56) References Cited

U.S. PATENT DOCUMENTS

| | | |
|---|---|---|
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,762,032 B1 | 7/2004 | Nelson et al. |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fuku |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,634,315 B2 | 12/2009 | Cholette |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,869 B1 | 1/2011 | Farazi |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,504,161 B1 | 8/2013 | Kornet et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |

(56) References Cited

U.S. PATENT DOCUMENTS

| | | |
|---|---|---|
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,203 B2 | 3/2019 | Faltys et al. |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 11,173,307 B2 | 11/2021 | Levine et al. |
| 11,207,518 B2 | 12/2021 | Huston et al. |
| 11,260,229 B2 | 3/2022 | Manogue |
| 11,278,718 B2 | 3/2022 | Faltys et al. |
| 11,311,725 B2 | 4/2022 | Levine et al. |
| 11,344,724 B2 | 5/2022 | Huston et al. |
| 11,383,091 B2 | 7/2022 | Faltys et al. |
| 11,406,833 B2 | 8/2022 | Faltys et al. |
| 11,471,681 B2 | 10/2022 | Zitnik et al. |
| 11,547,852 B2 | 1/2023 | Levine et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |

(56) References Cited

U.S. PATENT DOCUMENTS

| | | |
|---|---|---|
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0171405 A1 | 7/2009 | Craig |
| 2009/0177112 A1 | 7/2009 | Gharib et al. |
| 2009/0182388 A1* | 7/2009 | Von Arx ............... A61N 1/378 607/60 |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |

(56) References Cited

U.S. PATENT DOCUMENTS

| | | |
|---|---|---|
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1 | 7/2010 | Goldknopf et al. |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280500 A1* | 11/2010 | Skelton ............... A61B 5/7475 604/891.1 |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0009734 A1 | 1/2011 | Foley et al. |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0301658 A1 | 12/2011 | Yoo et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0296176 A1 | 11/2012 | Herbst |
| 2012/0302821 A1 | 11/2012 | Burnett |
| 2013/0013016 A1 | 1/2013 | Diebold |
| 2013/0018439 A1 | 1/2013 | Chow et al. |
| 2013/0066392 A1 | 3/2013 | Simon et al. |
| 2013/0066395 A1 | 3/2013 | Simon et al. |
| 2013/0071390 A1 | 3/2013 | Stadheim et al. |
| 2013/0150756 A1 | 6/2013 | Vitek et al. |
| 2013/0245718 A1 | 9/2013 | Birkholz et al. |
| 2013/0289385 A1 | 10/2013 | Lozano et al. |
| 2013/0317580 A1 | 11/2013 | Simon et al. |
| 2014/0046407 A1 | 2/2014 | Ben-Ezra et al. |
| 2014/0105255 A1 | 4/2014 | Kutner |
| 2014/0206945 A1 | 7/2014 | Liao |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0324118 A1 | 10/2014 | Simon et al. |
| 2014/0330335 A1 | 11/2014 | Errico et al. |
| 2015/0018728 A1 | 1/2015 | Gross et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0196767 A1 | 7/2015 | Ahmed |
| 2015/0202446 A1 | 7/2015 | Franke et al. |
| 2015/0233904 A1 | 8/2015 | Nayak |
| 2015/0241447 A1 | 8/2015 | Zitnik et al. |
| 2016/0089540 A1 | 3/2016 | Bolea |
| 2016/0250097 A9 | 9/2016 | Tracey et al. |
| 2016/0279435 A1 | 9/2016 | Hyde et al. |
| 2016/0331952 A1 | 11/2016 | Faltys et al. |
| 2016/0367808 A9 | 12/2016 | Simon et al. |
| 2017/0202467 A1 | 7/2017 | Zitnik et al. |
| 2017/0239484 A1 | 8/2017 | Ram Rakhyani et al. |
| 2017/0245379 A1 | 8/2017 | Kang |
| 2017/0254818 A1 | 9/2017 | Haskins et al. |
| 2017/0304621 A1 | 10/2017 | Malbert et al. |
| 2017/0361093 A1 | 12/2017 | Yoo et al. |
| 2018/0021580 A1 | 1/2018 | Tracey et al. |
| 2018/0078769 A1 | 3/2018 | Dinsmoor et al. |
| 2018/0085578 A1 | 3/2018 | Rennaker, II et al. |
| 2018/0117320 A1 | 5/2018 | Levine et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0054295 A1 | 2/2019 | Pannu et al. |
| 2019/0090358 A1 | 3/2019 | Aresta et al. |
| 2019/0192847 A1 | 6/2019 | Faltys et al. |
| 2020/0384259 A1 | 12/2020 | Chasensky et al. |
| 2021/0251848 A1 | 8/2021 | Tracey et al. |
| 2021/0315505 A1 | 10/2021 | Levine et al. |
| 2021/0353949 A1 | 11/2021 | Faltys et al. |
| 2022/0040483 A1 | 2/2022 | Levine et al. |
| 2022/0072309 A9 | 3/2022 | Levine et al. |
| 2022/0118257 A1 | 4/2022 | Huston et al. |
| 2022/0193413 A1 | 6/2022 | Levine et al. |
| 2022/0212001 A1 | 7/2022 | Faltys et al. |
| 2022/0212012 A1 | 7/2022 | Manogue |
| 2022/0257941 A1 | 8/2022 | Levine et al. |
| 2022/0280797 A1 | 9/2022 | Faltys et al. |
| 2022/0362555 A1 | 11/2022 | Zitnik et al. |
| 2023/0019961 A1 | 1/2023 | Huston et al. |
| 2023/0241387 A1 | 8/2023 | Levine et al. |
| 2023/0321445 A1 | 10/2023 | Zanos et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 A | 2/1910 |
| GB | 2073428 A | 10/1981 |
| JP | 2017502787 | 1/2017 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2015/009907 A1 | 1/2015 |
| WO | WO2016/134197 A1 | 8/2016 |

OTHER PUBLICATIONS

US 11,745,017 B2, 09/2023, Zanos et al. (withdrawn)

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

(56) References Cited

OTHER PUBLICATIONS

Antonica, A., et al., Vagal control of lymphocyte release from rat thymus, J. Auton. Nerv. Syst., vol. 48(3), pp. 187-197, Aug. 1994.
Asakura et al., Non-surgical therapy for ulcerative colitis, Nippon Geka Gakkai Zasshi, vol. 98, No. 4, pp. 431-437, Apr. 1997 (abstract only).
Beliavskaia et al., "On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.
Ben-Noun et al.; Neck circumference as a simple screening measure for identifying overweight and obese patients; Obesity Research; vol. 9; No. 8; pp. 470-477; Aug. 8, 2001.
Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression in shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. Vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, celular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, no. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioloigal aspects and therapeutic approaches, abstacts and program, Fourth international Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, ©1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
Crusz et al.; Inflammation and cancer; advances and new agents; Nature reviews Clinical Oncology; 12(10); pp. 584-596; doi: 10.1038/nrclinonc.2015.105; Jun. 30, 2015.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
De Jonge et al.; Stimulation of the vagus nerve attenuates macrophage activation by activating the Jak2-STAT3 signaling pathway; Nature Immunology; 6(8); pp. 844-851; Aug. 2005.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.

(56) References Cited

OTHER PUBLICATIONS

Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergio transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256; Winter 2011.
Emery et al.; Rituximab versus an alternative TNF inhibitor in patients with rheumatoid arthritis who failed to respond to a single previous TNF inhibitor: switch-ra, a global, oberservational, comparative effectiveness study; Annals of the Rheumatic Diseases; 4(6); pp. 979-964; Jun. 2015.
Engineer et al.; Directing neural plasticity to understand and treat tinnitus; Hear. Res.; 295; pp. 58-66; Jan. 2013.
Engineer et al.; Reversing pathological neural activity using targeted plasticity; Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotorny, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(-)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.
Gottenberg et al.; Non-TNF-targeted biologic vs a second anti-TNF drug to treat rheumatoid arthritis in patients with insufficient response to a first anti TNF drug: a randomized clinical trial; JAMA; 316(11); pp. 1172-1180; Sep. 2016.
Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; Jul. 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Housley et al.; Biomarkers in multiple sclerosis; Clinical Immunology; 161(1); pp. 51-58; Nov. 2015.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, MO, US, pp. 930-937, Nov. 1, 1999.
Jacob et al.; Detrimental role of granulocyte-colony stimulating factor in neuromyelitis optica: clinical case and histological evidence; Multiple Sclerosis Journal; 18(12); pp. 1801-1803; Dec. 2012.

(56) References Cited

OTHER PUBLICATIONS

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase, J. Virol., 76(13), pp. 6545-6557, Jul. 2002.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;,vol. 13; No. 2; pp. 93-122; Apr.-Jun. 1982.

Kanai, T. et al., Interleukin-18 and Crohn's disease, Digestion, vol. 63, suppl. 1, pp. 37-42; 2001 (year of pub. sufficiently earlier than effective US filing date and any foreign priority date).

Katagiri, M., et al., Increased cytokine production by gastric mucosa in patients with helicobacter pylori infection, J. Clin, Gastroenterol., vol. 25, Suppl. 1, pp. S211-S214, 1997.

Katsavos et al.; Biomarkers in multiple sclerosis: an up-to-date overview; Multiple Sclerosis International; vol. 2013, Article ID 340508, 20 pages; Jan. 1, 2013.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Kawashima, et al., Extraneuronal cholinergic system in lymphocytes, Pharmacology & Therapeutics, vol. 86, pp. 29-48, Apr. 2000.

Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.

Koopman et al.; Pilot study of stimulation of the cholinergic anti-inflammatory pathway with an implantable vagus nerve stimulation device in patients with rheumatoid arthritis; 2012 ACRIARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.

Koopman et al.; THU0237 first-in-human study of vagus nerve stimulation for rheumatoid arthritis: clinical and biomarker results through day 84; Annals of the Rheumatic Diseases: 72(Suppl 3):A245; Jun. 1, 2013 (Abstract Only).

Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.

Krarup et al.; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, Shock, vol. 5, No. 5, pp. 385-388, May 1996.

Kuznik, "Role of the vascular wall in the process of hemostatis," Usp Sovrem Biol., vol. 75(1): pp. 61-85; 1973 (the year of publication is sufficiently earlier than the effective U.S. filing date and any foreign priority date so that the particular month of publication is not in issue).

Kuznik, et al., "Blood Coagulation in stimulation of the vagus nerve in cats," Biull. Eskp. Biol. Med., vol. 78(7): pp. 7-9; 1974 (the year of publication is sufficiently earlier than the effective U.S. filing date and any foreign priority date so that the particular month of publication is not in issue).

Kuznik, et al., "Heart as an efferent regulator of the process of blood coagulation and fibrinolysis," Kardiologiia, vol. 13(3): pp. 10-17; 1973 (the year of publication is sufficiently earlier than the effective U.S. filing date and any foreign priority date so that the particular month of publication is not in issue).

Kuznik, et al., "Role of the heart and vessels in regulating blood coagulation and fibrinolysis," Kagdiologiia, vol. 13(4): pp. 145-154, Apr. 1973.

Kuznik, et al., "Secretion of blood coagulation factors into saliva under conditions of hypo-and hypercoagulation," Voprosy Meditsinskoi Khimii, vol. 19(1): pp. 54-57; 1973(the year of publication is sufficiently earlier than the effective U.S. filing date and any foreign priority date so that the particular month of publication is not in issue).

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158; 1975 (the year of publication is sufficiently earlier than the effective U.S. filing date and any foreign priority date so that the particular month of publication is not in issue).

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.

Lipton, J. M. et al.; Anti-inflammatory actions of the neuroimmunomodulator ?-MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).

(56) References Cited

OTHER PUBLICATIONS

Martindale: The Extra Pharmacopoeia; 28th Ed. London; The Pharmaceutical Press; pp. 446-485; ©1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.
McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Monaco et al.; Anti-TNF therapy:past,present, and future; International Immunology; 27(1); pp. 55-62; Jan. 2015.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Palov et al.; The cholinergic anti-inflammatory pathway: a missing link in neuroimmunomodulation; Molecular Medicine; 9(5); pp. 125-134; May 2003.
Pateyuk, et al., "Treatment of Botkin's disease with heparin," Klin. Med., vol. 51(3): pp. 113-117, Mar. 1973.
Pavlov et al.; The cholinergic anti-inflammatory pathway; Brain, Behavior, and Immunity; 19; p. 493-499; Nov. 2005.
Pavlov et al.; Controlling inflammation: the cholinergic anti-inflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504) ; Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al.; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology: 148(1-2); pp. 162-171; Mar. 2004.
Rendas-Baum et al.; Evaluating the efficacy of sequential biologic therapies for rheumatoid arthritis patients with an inadequate response to tumor necrosis factor -alpha inhibitors; Arthritis research and therapy: 13; R25; 15 pages; ; Feb. 2011.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiogram the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Rosas-Ballina et al.; Acetylcholine-synthesizing T cells relay neural signals in a vagus nerve circuit Science: 334(6052); pp. 98-101; 10 pages; (Author Manuscript); Oct. 2011.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sanchez et al.; The development and function of memory regulatory t cells after acute viral infections; J. Immunol.; 189(6); pp. 2805-2814; Sep. 15, 2012.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.

(56) References Cited

OTHER PUBLICATIONS

Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shevach et al.; Regulatory T cells; Nature Reviews Immunology; 1 page; ©2010 retrieved from internet (http://www.nature.com/nri/posters/tregcells/nri1001_treg_poster.pdf) on Aug. 11, 2016 (Poster).
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Strowig et al.; Inflammasomes in health and disease; Nature; vol. 481; pp. 278-286; doi: 10.1038/nature10759; Jan. 19, 2012.
Sugano et al., Nicotine inhibits the production of inflammatory mediators in U937 cells through modulation of nuclear factor-kappaß activation, Biochemical and Biophysical Research Communications, vol. 252, No. 1, pp. 25-28, Nov. 9, 1998.
Suter et al.; Do glial cells control pain ?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.

Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K. J.; Reflex control of immunity; Nat Rev Immunol; 9(6); pp. 418-428; Jun. 2009.
Tracey, K.J., The inflammatory reflex, Nature, vol. 420, pp. 853-859, Dec. 19-26, 2002.
Tsutsui, H., et al., Pathophysiologi inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 Dna polymerase; Science, 249(4968), pp. 505-510, Aug. 3, 1990.
Van Der Horst et al.; Stressing the role of FoxO proteins in lifespan and disease; Nat Rev Mol Cell Biol .; vol. 8; No. 6; pp. 440-450; Jun. 2007.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
vanWesterloo, et al., The cholinergic anti-inflammatory pathway regulates the host response during septic peritonitis, The Journal of Infectious Diseases, vol. 191, pp. 2138-2148, Jun. 15, 2005.
Venken et al.; Natural naïve CD4+ CD25+ CD127low regulatory T cell (Treg) development and function are disturbed in multiple sclerosis patients: recovery of memory treg homeostasis during disease progression; J. Immunol.; 180(9); pp. 6411-6420; May 2008.
Ventureyra, Transcutaneous vagus nerve stimulation for partial onset seizure therapy, Child's Nerv Syst, vol. 16(2), pp. 101-102, Feb. 2000.
Vida et al.; Aplha 7-cholinergic receptor mediates vagal induction of splenic norepinephrine; Journal of Immunology; 186(7); pp. 4340-4346; 16 pages; (Author Manuscript); Apr. 2011.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.

(56) References Cited

OTHER PUBLICATIONS

Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yang et al.; Acetylcholine inhibits LPS-induced MMP-9 production and ccell migration via the alpha7 nAChR-JAK2/STAT3 pathway in RAW264.7 cells; Cellular Physiology and Biochemistry; 36(5); pp. 2025-2038; (the year of publication is sufficiently earlier than the effective U.S. filing date and any foreign priority date so that the particular month of publication is not in issue) 2015.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhang et al.; Roles of SIRT1 in the acute and restorative phases following induction of inflammation.; J Biol Chem.; vol. 285; No. 53; pp. 41391-401; Dec. 2010.
Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.
Zitnik et al.; Treatment of chronic inflammatory diseases with implantable medical devices; Cleveland Clinic Journal of Medicine; 78(Suppl 1); pp. S30-S34; Aug. 2011.
Manogue; U.S. Appl. No. 18/150,177 entitled "Methods and apparatuses for reducing bleeding via coordinated trigeminal and vagal nerve stimulation," filed Jan. 4, 2023.
Huston et al.; U.S. Appl. No. 18/355,401 entitled "Methods for reducing bleeding in hemophilia by vagus nerve stimualtion to prime platelets," filed Jul. 19, 2023.
Yang et al.; Axon myelination and electrical stimulation in a microfluidic, compartmentalized cell culture platform; Neuromolecular medicine; vol. 14; pp. 112-118; Jun. 2012.
Gautron et al.; Neurobiology of inflammation-associated anorexia; Frontiers in Neuroscience; 3(59); 10 pages; Jan. 8, 2010.

* cited by examiner

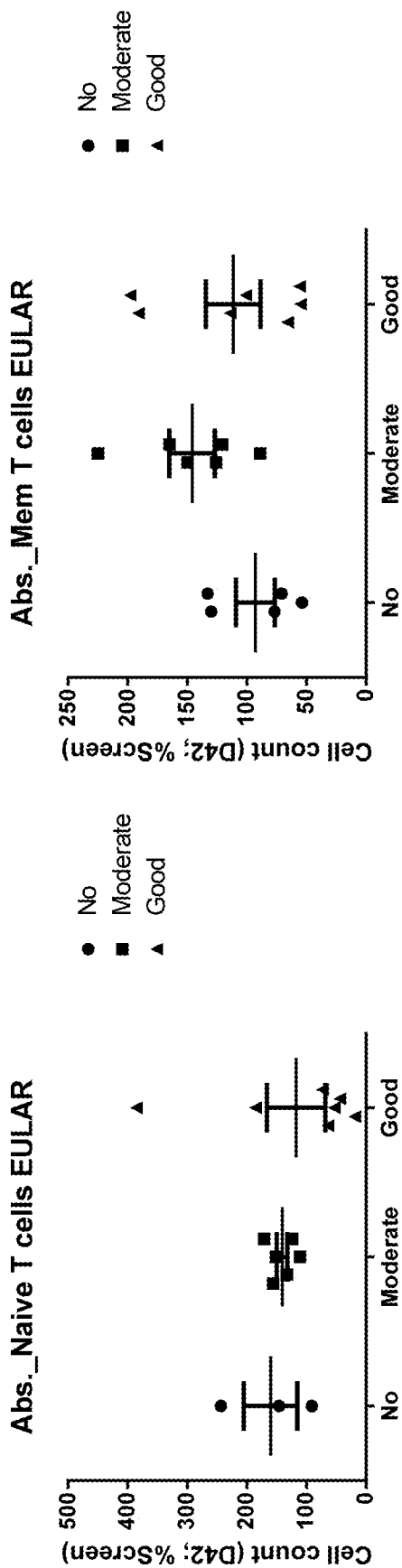

CONTROL OF VAGAL STIMULATION

CROSS REFERENCE TO RELATED APPLICATIONS

This application is a continuation of U.S. patent application Ser. No. 16/916,036, filed Jun. 29, 2020, titled "CONTROL OF VAGAL STIMULATION," now U.S. Pat. No. 11,547,852, which is a continuation of U.S. patent application Ser. No. 15/411,933, filed Jan. 20, 2017, titled "CONTROL OF VAGAL STIMULATION," now U.S. Pat. No. 10,695,569, which claims priority to U.S. Provisional Patent Application No. 62/281,135, titled "SYSTEMS AND METHODS FOR MODULATING T-REGULATORY CELLS USING VAGUS NERVE STIMULATION," filed on Jan. 20, 2016; U.S. Provisional Patent Application No. 62/286,950, titled "USER INTERFACE FOR IMPLANTED NEUROSTIMULATOR," filed on Jan. 25, 2016; U.S. Provisional Patent Application No. 62/286,957, titled "ADAPTIVE CLOSED-LOOP CONTROL OF VAGAL STIMULATION," filed on Jan. 25, 2016; and U.S. Provisional Patent Application No. 62/340,950, titled "ADAPTIVE CLOSED-LOOP CONTROL OF VAGAL STIMULATION," filed on May 24, 2016. Each of these applications is herein incorporated by reference in its entirety.

This application may also be related to one or more of: U.S. patent application Ser. No. 14/887,192, titled "NEURAL STIMULATION DEVICES AND SYSTEMS FOR TREATMENT OF CHRONIC INFLAMMATION", filed on Oct. 19, 2015, Publication No. US-2016-0038745-A1; U.S. patent application Ser. No. 14/931,711, titled, "NERVE CUFF WITH POCKET FOR LEADLESS STIMULATOR", filed on Nov. 3, 2015, Publication No. US-2016-0051813-A1; U.S. patent application Ser. No. 14/968,702, titled, "SINGLE-PULSE ACTIVATION OF THE CHOLINERGIC ANTI-INFLAMMATORY PATHWAY TO TREAT CHRONIC INFLAMMATION", filed on Dec. 14, 2015, Publication No. US-2016-0096017-A1; U.S. patent application Ser. No. 13/338,185, titled "MODULATION OF SIRTUINS BY VAGUS NERVE STIMULATION", filed on Dec. 27, 2011, Publication No. US-2013-0079834-A1; and U.S. patent application Ser. No. 14/782,715, titled "CLOSED-LOOP VAGUS NERVE STIMULATION", filed on Oct. 6, 2015, Publication No. US-2016-0067497-A1. Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Embodiments of the invention relate generally to neuromodulation of the vagus nerve for the treatment of inflammation.

BACKGROUND

Some neuromodulation devices have the ability to modulate their own stimulation settings quickly based on immediate feedback from target tissue (e.g. muscle) that they are stimulating, since the target tissue responds quickly to stimulation. For example, electromyography (EMG) can be used to record and evaluate the electrical activity of muscles, which provides information regarding the activation level and/or recruitment of the muscles. This information can be processed and used to modulate the neurostimulation parameters applied to the muscles, thereby improving the efficacy of the stimulation device.

Vagus nerve stimulation (VNS) for the treatment of chronic inflammatory diseases, on the other hand, is not easily programmed for optimal result, as decreases in inflammation take hours to days to manifest. Consequently, it would be desirable to identify alternative markers or surrogates that indicate activation of the cholinergic anti-inflammatory pathway by VNS. In addition, it would be desirable to use these alternative markers or surrogates to identify patients that may be suitable for receiving VNS therapy. Furthermore, it would be desirable to directly modulate these markers or surrogates as an alternative or supplemental way to treat inflammation.

SUMMARY OF THE DISCLOSURE

In general, described herein are methods and apparatuses (including devices, systems, implants, etc.) for treatment of inflammatory disorders. In particular, described herein are methods of using one or more patient metrics (e.g., biomarkers) alone or, in particular, in combination, to determine if a patient is a good candidate for vagus nerve stimulation and/or to modify or modulate the therapeutic stimulation applied.

For example, described herein are methods for screening or prescreening a patient to determine if the patient is a good candidate for implantable vagus nerve stimulation, prior to stimulation. In general, a metric (e.g., biomarker, such as regulatory T cell level, inflammatory biomarker signal, heart rate variability, etc.) may be taken prior to a vagus nerve stimulation (either internal or external) to provide a baseline value of the one or more metrics, and a vagus nerve stimulation (such as a VNS that would typically result in a modulation of inflammation in a typically responsive patient) may be applied and the same metric(s) taken from the patient immediately or at one or more time intervals thereafter (e.g., within the first hour, 2 hours, 3 hours, 4 hours, 5 hours, 6 hours, 7 hours, 8 hours, 9 hours, 10 hours, 12 hours, 16 hours, 20 hours, 24 hours, 36 hours, 40 hours, 48 hours, 3 days, 4 days, 5 days, 6 days, 7 days, 8 days, 9 days, 10 days, one month, 2 months, three months, etc.). The baseline and post-VNS results may be compared. Alternatively, a running level of the one or more metrics may be monitored to modulate the applied VNS.

When used as a screening technique, a patient may be determined to be a responder (high responder, moderate responder, low responder and/or non-responder) and thereafter stimulated at an appropriate level based on a comparison between one or more baseline metrics to the metrics following vagus nerve stimulation of the patient, or an alternative or supplemental therapy may be applied. The vagus nerve stimulation may be applied externally and/or non-invasively, e.g., by ultrasound or other mechanical stimulation, transcutaneously, including electrically, magnetically (e.g., TES), etc., or invasively, including via one or more needle electrode or the like. Insertion and/or implantation may therefore be performed based on the magnitude of the response.

In addition, vagus nerve stimulation may be set or modified for a patient based on feedback from one or more (and particularly combinations of) metrics. Described herein are biomarker metrics, such as memory T cell levels, as well as physiological markers, and/or activity markers. Physiological markers may include heart rate and/or hear rate variability, and activity markers may include one or more activity level. In particular, described herein are apparatuses adapted to received and/or record metrics that may be used to set, adjust or modify stimulation parameters in a closed loop, semi-closed loop, and/or open loop manner. Any of the vagus nerve stimulators (neurostimulators) described herein may be adapted to determine, record or receive metrics from one or more biomarker, activity level or physiological marker, and may store, transmit, analysis, and/or apply control logic to adjust the behavior of the vagus nerve stimulator based on the one or more metrics measured from the patient.

For example, described herein are methods and apparatuses for treatment of inflammation using vagus nerve stimulation (VNS). In some variations, the one or more metrics used to screen a patient to determine if they would benefit from an implantable neurostimulator, or to modulate or modify the activity of an implanted neurostimulator in a patient having a device, may include the level or ratio of regulatory T cells. Regulatory T cells constitute one immune regulatory cell population in the body. Tregs cells can be characterized broadly into two groups, naïve Tregs (nTregs), and memory Tregs (mTregs). nTregs are precursors to mTregs that have not yet been exposed to their cognate antigen(s). Once nTregs have been exposed to their cognate antigen(s), they can become activated and may further develop into mTregs. mTregs can suppress and/or down regulate the immune response, including the inflammatory response, by secreting various suppressive cytokines and molecules that act on effector T cells and dendritic cells.

VNS has been shown to generally be effective in reducing inflammation. Surprisingly, the inventors have herein found that, in some subjects, the application of VNS also increases the amount of mTregs. The increase in mTregs is surprising because VNS has been shown to reducing inflammation and Treg cells are typically activated in response to inflammation. In those subjects where the application of VNS increased their blood concentration of mTregs (termed moderate or good responders), they also noted an improvement of their inflammation symptoms compared to individuals in which the application of VNS did not affect their concentration of mTregs (relative to nTregs) and VNS may also not have greatly increased their inflammation symptoms; these individuals were labeled non-responders.

Thus, in one example of a method of screening patients may include examining the patients Regulatory T cell response before (baseline) and after vagus nerve stimulation. For example, described herein are methods of preliminary testing of subjects for their potential responsiveness to VNS therapy prior to implanting an implantable stimulation device. Preliminary test may be largely non-invasive or minimally-invasive and may include, e.g., either mechanical or electrical stimulation to a region of the subject's body that would stimulate a branch of the vagus nerve. A baseline of the subject's Treg cell concentration may be obtained. Qualitative evaluation of the subject's inflammation symptoms may also be recorded. After applying the VNS, a measure of the subject's Treg cells concentration may be determined. Additional assessment of the subject's inflammation symptoms may also be evaluated. Candidate for whom a robust Treg response is seen may be implanted. Further the initial stimulation level may be set based in part on the results of the metric (e.g., Treg cell effect); more robust responders may have lower and/or less frequent stimulation applied, while less robust responders may have higher and/or more frequent stimulation applied. Upon determination that the subject is a viable candidate for VNS, the microstimulator may be implanted around a cervical portion of the subject's vagus nerve. The microstimulator may be rechargeable using a charger configured to be worn around the subject's neck, for example. VNS may be applied in a predetermined regimen and repeated over a course of days or weeks. The concentration of the subject's Treg cells may be recorded and the subject's inflammation symptoms may also be accessed.

In some embodiments, a method for treating chronic inflammation in a subject is provided. The method can include stimulating the subject's vagus nerve with an electrical stimulation; modulating a level of memory T regulatory cells in the subject with the electrical stimulation; and reducing a level of inflammation in the patient.

In some embodiments, the method further includes obtaining a baseline level of memory T regulatory cells in the subject; and obtaining a post-stimulation level of memory T regulatory cells in the subject.

In some embodiments, the method further includes comparing the baseline level of memory T regulatory cells to the post-stimulation level; and adjusting at least one parameter of the electrical stimulation based on the step of comparing the baseline level of memory T regulatory cells to the post-stimulation level.

In some embodiments, the at least one parameter is adjusted until the post-stimulation level is greater than the baseline level by at least a predetermined amount.

In some embodiments, the predetermined amount is 10 percent.

In some embodiments, the step of adjusting at least one parameter of the electrical stimulation includes increasing the amplitude of the electrical stimulation.

In some embodiments, the electrical stimulation is delivered from an implanted microstimulator.

In some embodiments, the electrical stimulation is delivered from a transcutaneous electrical nerve stimulator.

In some embodiments, a method for screening a subject for suitability for vagus nerve stimulation treatment is provided. The method can include obtaining a baseline level of memory T regulatory cells in the subject; stimulating the subject's vagus nerve; obtaining a post-stimulation level of memory T regulatory cells in the subject; and comparing the baseline level to the post-stimulation level to determine whether the subject is suitable for vagus nerve stimulation treatment.

In some embodiments, the step of comparing the baseline level to the post-stimulation level includes determining whether the post-stimulation level exceeds the baseline level by a predetermined amount.

In some embodiments, the predetermined amount is at least 10 percent.

In some embodiments, the step of obtaining a baseline level of memory T regulatory cells includes determining the number of CD4+CD25+CD127LowCD45RO+ cells in a sample of blood from the subject.

In some embodiments, the step of obtaining a baseline level of memory T regulatory cells includes determining the expression of FOXP3 in a sample of blood from the subject.

In some embodiments, the step of stimulating the subject's vagus nerve comprises noninvasively stimulating the vagus nerve.

In some embodiments, the noninvasive stimulation is electrical stimulation.

In some embodiments, the noninvasive stimulation is mechanical stimulation.

In some embodiments, the mechanical stimulation is performed on the patient's ear.

In some embodiments, the step of stimulating the subject's vagus nerve comprises minimally invasively stimulating the vagus nerve.

In some embodiments, the minimally invasive stimulation includes stimulation from a needle electrode.

In some embodiments, the method further includes implanting a vagus nerve stimulator in the subject based at least in part on the step of comparing the baseline level to the post-stimulation level.

In some embodiments, a method of setting a dosage level for electrically stimulating a subject's vagus nerve for treating inflammation is provided. The method can include measuring a baseline level of memory T regulatory cells in a sample of the subject's blood; stimulating the subject's vagus nerve with an electrical stimulation; measuring a post-stimulation level of memory T regulatory cells in a sample of the patient's blood taken after the step of stimulating the subject's vagus nerve; comparing the baseline level of memory T regulatory cells to the post-stimulation level; and adjusting at least one parameter of the electrical stimulation based on the step of comparing the baseline level of memory T regulatory cells to the post-stimulation level.

In some embodiments, the at least one parameter is adjusted until the post-stimulation level is greater than the baseline level by at least a predetermined amount.

In some embodiments, the step of adjusting at least one parameter of the electrical stimulation includes increasing the amplitude of the electrical stimulation.

The methods and apparatuses described herein may include or be adapted for modulation of a therapeutic stimulation applied by any of the neurostimulator (e.g., microstimulator, microregulators, MRs, etc.) described herein based on one or more sensors detecting body activity and/or personal wellness. For example, described herein apparatuses (devices and systems) adapted to receive information about body movement (body motion, heart rate, HRV, etc.) and/or wellness (subjective, patient reported) and this information may be used to modulate the VNS applied by the apparatus.

In some variations the implant includes one or more sensor (e.g., accelerometers) that may be adapted for use in a control as described herein, including closed-loop, semi-closed loop, or open-loop (e.g., in which a patient, physician and/or technician may receive information on the metric to help guide or suggest treatment options). In some variations, the apparatus may receive information from other sources of data, including third-party databases. This data may be received by the implant and/or charger and/or programmer/controller (or a device integrating two or more of these functions) and may be used to calculate a modification of the current/ongoing VNS protocol and/or to initiate and/or to terminate the application of a VNS protocol.

Any of the apparatuses described herein may be adapted or configured to use hear rate variability (HRV) as a metric alone or in combination with other metrics. Heart rate variability may be measured from the same electrodes applying the VNS of the microstimulator. Surprisingly, although the electrodes are in electrical contact with the nerve, the inventors have herein shown that an electrocardiograph (ECG) signal, and particularly the R peak of the signal, may be recorded from the electrodes of a microstimulator (e.g., across a bipolar electrode on the vagus) within the nerve cuff holding the microstimulator to the cervical vagus nerve. Thus, HRV may be determined in a patient at various times before and immediately after VNS using a microstimulator connected to the vagus nerve by appropriately filtering (e.g., high pass filtering at an appropriate frequency such as 10 Hz) and analysis of a recorded signal. Alternatively or additionally, HRV may be determined by the use of an accelerometer, a microphone, or the like, which may also be included as part of the microstimulator. In some variations, a separate measure of a metric (including, but not limited to HRV) may be determined using a device that is separate from the microstimulator, and this data may be fed to the microstimulator or to a device in communication (e.g., remote controller) with the microstimulator.

For example, when HRV is used to modulate activity and/or screen a patient, the VNS may be modulated by increasing or decreasing the frequency and/or intensity of stimulation based on HRV. Heart rate variability may be determined by the implant, or by a controller in communication with the implant (e.g., smartwatch, smartphone, etc.), and may be continuously or periodically determined. In particular the apparatuses described herein may be configured to determine HRV for a patient when the patient is at rest; thus, the measure of HRV may be taken based on one or more of: time of day and/or patient activity level. For example, the HRV measure may be taken when the patient is not moving (e.g., sleeping, etc.) based on an internal or external accelerometer or any other motion/vibration monitor in communication with the apparatus. Alternatively or additionally, the apparatus may be configured to determine HRV a fixed time period (or within a predetermined window of time) following VNS, such as within 1-120 minutes, within 2-100 minutes, etc. following VNS, and/or when the patient is at rest following this stimulation, which may be determined or confirmed by an activity monitor.

Alternatively or additionally, respiratory information may be measured by an implantable apparatus and used a metric or in conjunction with any of the metrics described herein. For example, if an accelerometer is included in the device, respiratory movements and/or sounds may be used to p provide a measure of respiratory rates.

Also described herein are methods for treating inflammation in a subject based on one or more of the metrics (e.g., heart rate, activity, body temperature, etc.) described herein. For example, described herein are methods for treating inflammation comprising: measuring a first heart rate variability from the subject using an electrode of an implantable microstimulator, wherein the electrode is in electrical contact with the subject's vagus nerve; applying a first electrical stimulation to the subject's vagus nerve from the electrode; measuring a second heart rate variability from the subject after the first electrical stimulation; and applying a second electrical stimulation to the subject's vagus nerve based on the first heart rate variability and the second heart rate variability.

The method may also include measuring a second metric from the patient, and further wherein applying the second electrical stimulation is based on the first heart rate variability, the second heart rate variability and the second metric. The second metric may comprise one or more of: temperature, activity, cytokine level, and memory T cell level. Applying the second electrical stimulation to the subject may comprise increasing or decreasing the stimulation based on the first heart rate variability and the second heart rate variability, wherein increasing or decreasing the stimulation may comprise increasing or decreasing one or more of: the frequency of stimulation, the duration of stimulation, the burst duration, the amplitude of electrical stimulation, and the peak-to-peak voltage of the stimulation.

Applying the second electrical stimulation to the subject's vagus nerve based on the first heart rate variability and the second heart rate variability may comprise determining a ratio of high frequency to low frequency components of heart rate variability. The method of claim 1, wherein the second electrical stimulation is applied after an off-period of between 30 minutes and 24 hours. The electrode may be in contact with the subject's vagus nerve in the patient's cervical region. The low frequency (LF) band (e.g., approximately 0.04-0.15 Hz) may be related to both sympathetic and parasympathetic modulation, and the high frequency (HF) band (e.g., approximately 0.15-0.40 Hz, or 0.18 to 0.4 Hz) may be governed almost exclusively by parasympathetic effects. The ratio of LF to HF power may be used as a metric of sympathetic/parasympathetic balance. It is important to note, however, that a driver of HRV in the HF band may be respiration. The magnitude of HF power may be highly dependent on the depth of respiration, which often varies greatly from one recording epoch to another. HRV may also be referred to as "cycle length variability", "RR variability" (where R is a point corresponding to the peak of the QRS complex of the ECG wave; and RR is the interval between successive Rs), and "heart period variability". HRV may be estimated by frequency domain (e.g., Fourier transform, including FFT) or time-domain methods (e.g., standard deviation of beat-to-beat intervals, root mean square of successive differences between adjacent beat-to-beat intervals, standard deviation of successive differences between adjacent beat-to-beat intervals, etc.

Also described herein are leadless, implantable microstimulator apparatus for treating chronic inflammation in a patient, the apparatus comprising: a housing having a channel through which a nerve may pass; at least two electrically conductive contacts; a motion sensor within the housing, the motion sensor configured to measure physical activity of the patient; a power source (e.g., battery, capacitor, etc.) within the housing; an electronic assembly within the housing, wherein the electronic assembly comprises a controller configured to apply stimulation to the vagus nerve from the electrically conductive contacts and to measure heart rate variability from the electrically conductive contacts; further wherein the controller is configured to adjust the applied stimulation based on the measurement of heart rate variability; and a protection an orientation (POD) cuff configured to hold the housing over the nerve so that the nerve is in electrical communication with the electrically conductive contacts. The the motion sensor may comprise an accelerometer.

The controller may be configured to adjust the stimulation based on the measurement of heart rate variability and the measured physical activity. The controller may be configured to measure heart rate variability when the patient is at rest based on the motion sensor. Based on the measurement of heart rate variability, the controller may adjust one or more of: a stimulation amplitude, a stimulation duration, and a stimulation frequency of application. The controller may be configured increase one or more stimulation parameters when a decrease in physical activity is measured by the accelerometer.

Also described herein are methods for treating inflammation in a subject, the method comprising: measuring a first level of memory T regulatory cells in the subject; applying a first stimulation to the subject's vagus nerve; measuring a second level of memory T regulatory cells in the subject after the first stimulation; and applying a second stimulation to the subject's vagus nerve based on the first and second levels of memory T regulatory cells measured.

The method may also include comparing the first level of memory T regulatory cells to the second level of memory T regulatory cells. The second stimulation may be greater than than the first stimulation by at least a predetermined amount in one or more of: the frequency of stimulation, the duration of stimulation, the burst duration, the amplitude of electrical stimulation, and the peak-to-peak voltage of the stimulation. The second stimulation may be less than than the first stimulation by at least a predetermined amount in one or more of: the frequency of stimulation, the duration of stimulation, the burst duration, the amplitude of electrical stimulation, and the peak-to-peak voltage of the stimulation. The predetermined amount may be approximately 5%, 10%, 15%, 20%, 25%, 30%, 35%, 40%, 50%, 60%, 70%, 80%, 90%, 100%, etc.

Applying the second stimulation to the subject's vagus nerve may comprise applying electrical stimulation from an implanted microstimulator. Applying the first stimulation to the subject's vagus nerve may comprise applying a non-invasive stimulation to the subject's vagus nerve.

Measuring the first (and/or second) level of memory T regulatory cells may comprises determining a level of CD4+ CD25+CD127LowCD45RO+ cells in a sample of blood from the subject. Measuring the first and/or second level of memory T regulatory cells may comprise determining a level of expression of FOXP3 in a sample of blood from the subject.

Applying the first stimulation to the subject's vagus nerve may comprises applying a minimally-invasive stimulation to the subject's vagus nerve. For example, the minimally invasive stimulation may comprise stimulation from a needle electrode.

Also described here are methods of setting a dosage level for electrically stimulating a subject's vagus nerve for treating inflammation, the method comprising: measuring a baseline level of memory T regulatory cells in a sample of the subject's blood; applying a first stimulation to the subject's vagus nerve; measuring a post-stimulation level of memory T regulatory cells in a sample of the patient's blood taken after applying the first stimulation to the subject's vagus nerve; comparing the baseline level of memory T regulatory cells to the post-stimulation level; adjusting at least one parameter of the first stimulation based on the baseline level of memory T regulatory cells and the post-stimulation level of memory T regulatory cells; and applying a second stimulation to the subject's vagus nerve using the adjusted at least one parameter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8A-8F show comparisons of the cell count for both nTreg compared to mTregs as broken down into non-responder, moderate responder, and good responder categories using a EULAR and an ACR scale.

In FIG. 13, a change in the relative frequency components of HRV (e.g., low frequency and high frequency components) from baseline during a treatment period are shown for treatment of a model inflammatory disorder (Chron's disease). In this example, 5 minute epochs were analyzed at baseline and 2 time points during the therapy period, but not during active stimulation.

DETAILED DESCRIPTION

Vagus nerve stimulation (VNS) has been shown to modulate a variety biological processes in the body, including the inflammatory response. Although VNS stimulation may modulate the inflammatory response in some or most patients, the level of response to the patient may vary based on the applied VNS. A variety of techniques can be used to attempt to better identify or predict which patients may respond better to VNS. For example, the level of cytokines can be measured before and after VNS in an assay on the patient's blood or in a cell based assay. A reduction in the level or release of an inflammatory cytokine, such as TNF for example, may indicate that the patient is responding to VNS, and/or may give an indication of the level of response.

Described herein are methods and apparatuses in which one or more metrics, including biomarker metrics, activity metrics, physiological metrics, or the like, may be used to determine which patients may be treated by VNS and/or the dose or level of applied VNS either initially and/or in an ongoing manner. Thus, described herein are apparatuses (devices, systems, implants, etc.) for detecting one or more metric and for modulating a VNS therapy to treat an inflammatory disorder based on the one or more metric.

Vagus Nerve Stimulation System

Systems for electrically stimulating one or more nerves to treat chronic inflammation may include an implantable, wireless microstimulator such as those described herein and an external charging device (which may be referred to as a charging wand, charger, or energizer). In some variations the system also includes a controller (sometimes referred to herein as a "prescription pad", which may be an external processor in communication with the implanted microstimulator, such as a smartphone, smartwatch, etc.) that helps control and regulate the dose delivered by the system. The microstimulator may be secured in position using a securing device (which may be referred to as a "POD") to hold the microstimulator in position around or adjacent to a nerve. These microstimulator s may be designed and adapted for treatment of chronic inflammation, and may be configured specifically for such use. Thus, an implantable microstimulator may be small, and adapted for the low duty-cycle stimulation to modulate inflammation. For example, the implantable microstimulator may hold a relatively small amount of power over weeks or even months and discharge it at a rate sufficient to modulate the anti-inflammatory pathway without significantly depressing heart rate or triggering any number of unwanted effects from the vagus nerve or other neural connections. Any of the nerves of the inflammatory reflex, including the vagus nerve, may be treated as described herein using the systems described.

Figure 1A:
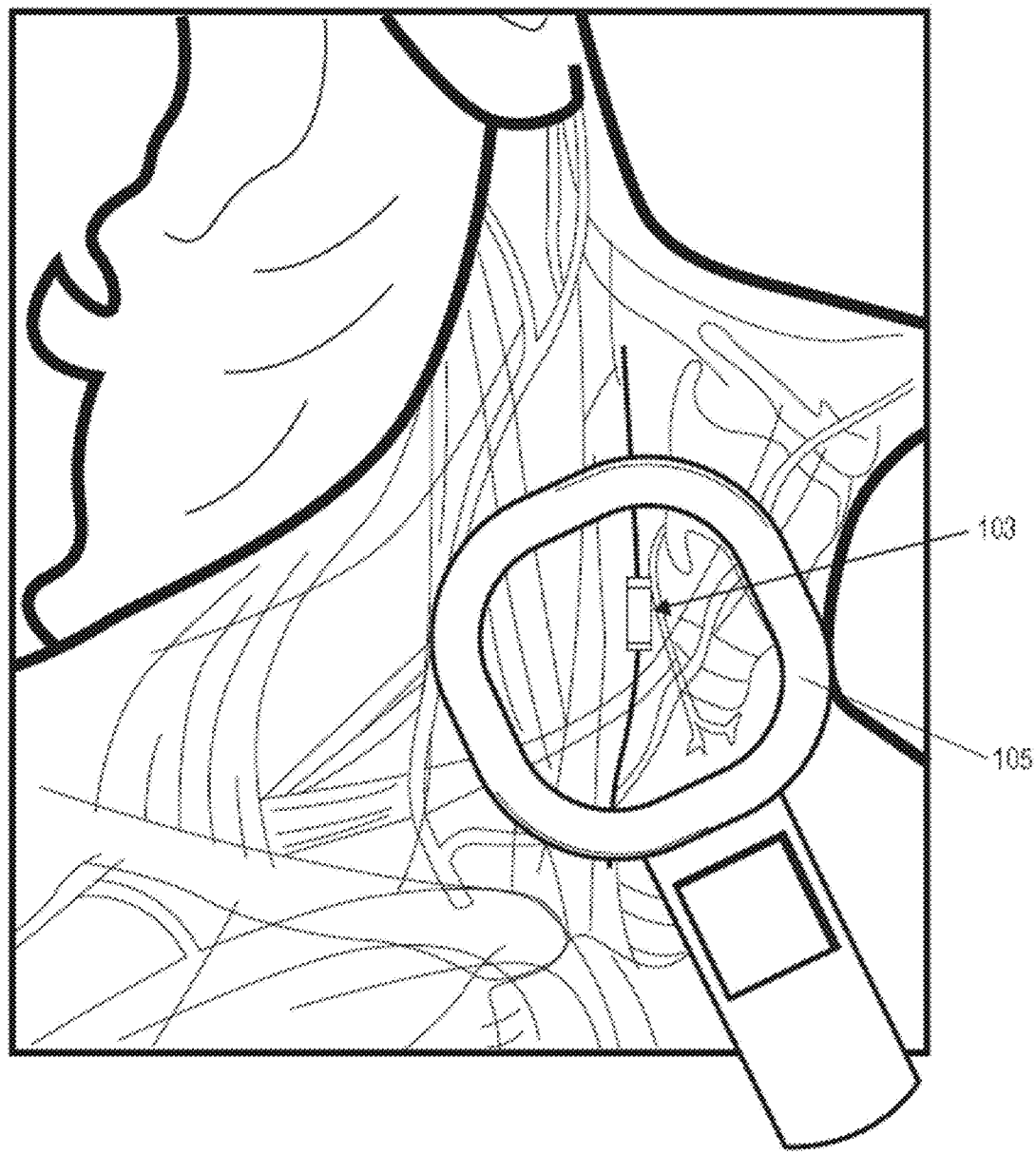
FIG. 1A shows one variation of a system for modulating chronic inflammation including a leadless microstimulator (shown connected to the vagus nerve) and an external charger/controller.

For example, FIG. 1A illustrates one variation of a system for treating chronic inflammation that includes a microstimulator contained in POD that is attached over or on cervical vagus nerve and charged and/or programmed by an external charger/programmer unit. This variation of a system includes a microstimulator 103 that has been implanted to contact the vagus nerve as shown. The implant may be programmed, controlled and/or charged by a charger/controller 105 device. In this variation the charger/controller is a loop with a wand region, alternatively a collar other charging device/applicator may be used.

Figure 1B:
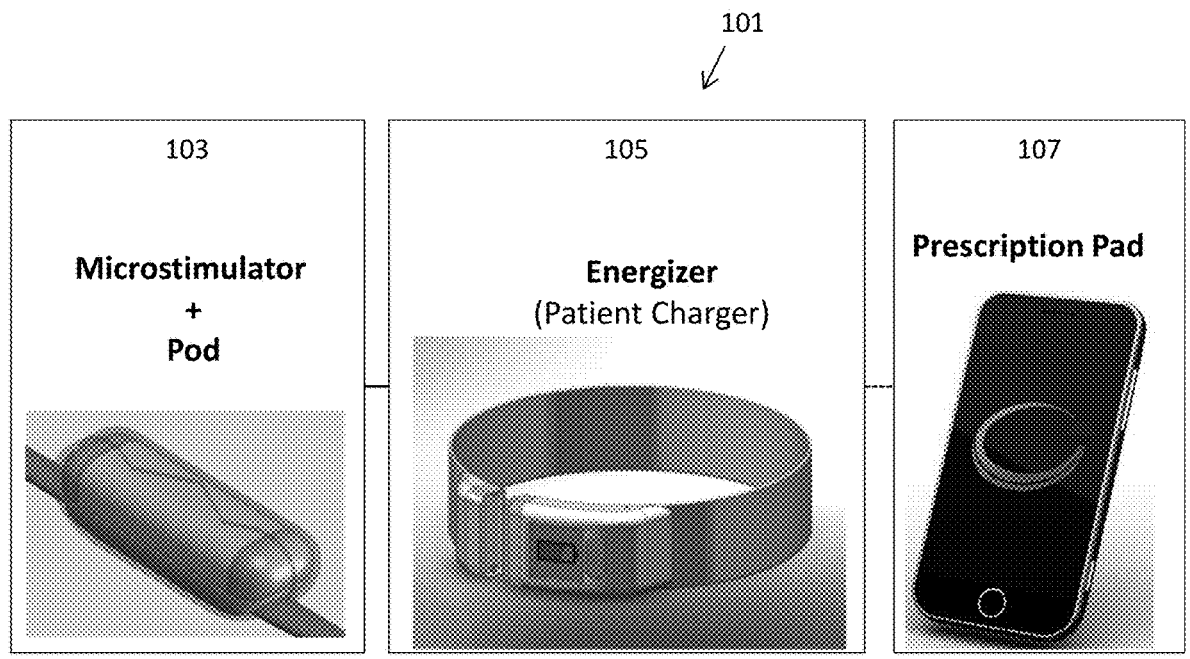
FIG. 1B shows another variation of a system for modulating chronic inflammation, including a microstimulator, charger ("energizer"), and system programmer/controller ("prescription pad").

FIG. 1B shows an example of a system for treating chronic inflammation that also includes an implantable microstimulator 103 (shown inserted into a POD to hold it in position relative to a nerve) and a charging device ("energizer" 105) configured as a collar to be worn around the subject's neck and charge the implant. Optionally, the system may include a prescription pad 107 which may be a separate dedicated device or part of a mobile or other handheld device (e.g., an application to run on a handheld device).

Figure 1C:
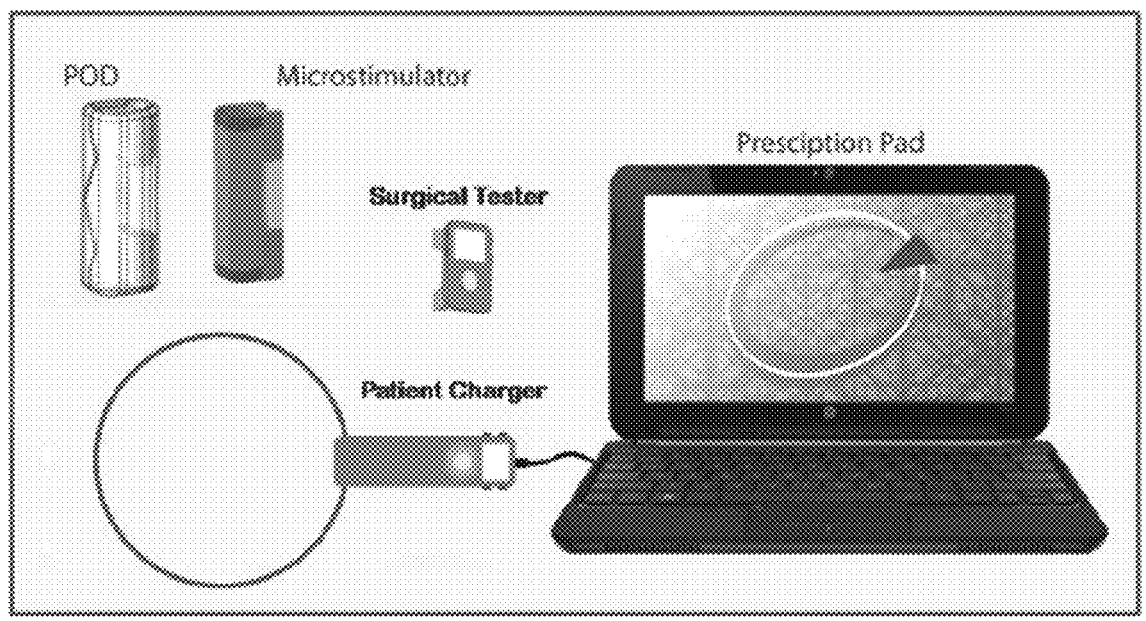
FIG. 1C shows another variations of a system for modulating chronic inflammation, including a microstimulator, a securing device (POD) for securing the leadless stimulator to the nerve, an external charger, a system programmer/controller ("prescription pad") and an optional surgical tester.

FIG. 1C shows another variation of a system for treating chronic inflammation. The systems described herein may also be referred to as systems for the neural stimulation of the cholinergic anti-inflammatory pathway (NCAP). These systems may be configured as chronic implantable systems. In some variations, the systems are configured to treat acutely (e.g., acute may 8 hours or less), sub-acutely (expected to occur for fewer than 30 days), or chronically (expected to occur for more than 30 days).

In general, the systems described herein may be configured to apply electrical stimulation at a minimum level necessary to modulate the inflammatory reflex (e.g., modulating cytokine release) characterized by the Chronaxie and rheobase. Chronaxie typically refers to the minimum time over which an electric current double the strength of the rheobase needs to be applied in order to stimulate the neuron. Rheobase is the minimal electrical current of infinite duration that results in an action potential. As used herein, cytokines refer to a category of signaling proteins and glycoproteins that, like hormones and neurotransmitters, are used extensively in cellular communication.

The NCAP Systems described herein are typically intended for the treatment of chronic inflammation through the use of implanted neural stimulation devices (microstimulators) to affect the Neural Stimulation of the Cholinergic Anti-inflammatory Pathway (NCAP) as a potential therapeutic intervention for rheumatologic and other inflammation-mediated diseases and disorders. Neurostimulation of the Cholinergic Anti-inflammatory Pathway (NCAP) has been shown to modulate inflammation. Thus, the treatment and management of symptoms manifested from the onset of disease (e.g., inflammatory disease) is based upon the concept of modulating the Cholinergic Anti-inflammatory Pathway. The NCAP pathway normally maintains precise restraint of the circulating immune cells. As used herein, the CAP is a reflex that utilizes cholinergic nerve signals traveling via the Vagus nerve between the brain, chemoreceptors, and the reticuloendothelial system (e.g., spleen, liver). Local release of pro-inflammatory cytokines (e.g., tumor necrosis factor or TNF) from resident immune cells is inhibited by the efferent, or indirectly by afferent vagus nerve signals. NCAP causes important changes in the function and microenvironment of the spleen, liver and other reticuloendothelial organs. Leukocytes which circulate systemically become "educated" as they traverse the liver and spleen are thereby functionally down regulated by the affected environment of the reticuloendothelial system. This effect can potentially occur even in the absence of an inflammatory condition.

Under this model, remote inflammation is then dampened by down-regulated cytokine levels. Stimulation of the vagus nerve with a specific regiment of electrical pulses regulates production of pro-inflammatory cytokines. In-turn, the down regulation of these cytokines may reduce localized inflammation in joints and other organs of patients with autoimmune and inflammatory disorders. Furthermore, as will be described in greater detail herein, it appears that VNS, in a subset of patients, has the added beneficial effect of promoting $CD4^+CD25^+Foxp3^+$ Treg cells that may lead to new methods of treating autoimmune disorders and mitigating tissue rejection in organ transplant cases.

The NCAP System includes a neurostimulator that may trigger the CAP by stimulating the cervical vagus nerve. The NCAP System issues a timed burst of current controlled pulses with sufficient amplitude to trigger the CAP at a particular interval. These two parameters, Dose Amplitude and Dose Interval, may be used by a clinician to adjust the device. For example, the clinician may set the Dose Amplitude by modifying the current level. The Dose Interval may be set by changing the duration between Doses (e.g. 12, 24, 48 hours).

In some variations, dose amplitude may be set to within the Therapy Window. The Therapy window is defined as the lower limit of current necessary to trigger the CAP, and the upper limit is the level at which the Patient feels uncomfortable. The lower limit is called the Threshold (T), and the uncomfortable level is called Upper Comfort Level (UCL).

Dose Amplitude thresholds are nonlinearly dependent upon Current (I), Pulse width (PW), Pulse Frequency (PF), and Burst Duration (BD). Amplitude is primarily set by charge (Q), that is Current (I)×Pulse width (PW). In neurostimulation applications current has the most linear relationship when determining thresholds and working within the therapy window. Therefore, the clinician may modify Dose Amplitude by modifying current. The other parameters are held to experimentally determined defaults. Pulse width is selected to be narrow enough to minimize muscle recruitment and wide enough to be well above the chronaxie of the targeted neurons. Stimulus duration and pulse frequency was determined experimentally in Preclinical work.

Dose Interval may be specific for particular diseases and the intensity of diseases experienced by a patient. Our initial research has indicated that the cervical portion of the vagus nerve may be an ideal anatomic location for delivery of stimulation. The nerve runs through the carotid sheath parallel to the internal jugular vein and carotid artery. At this location, excitation thresholds for the vagus are low, and the nerve is surgically accessible. We have not found any significant difference in biomarker modulation (e.g., modulation of cytokines) between right and left. Even though the right vagus is thought to have lower thresholds than the left in triggering cardiac dysrythmias, the thresholds necessary for NCAP are much lower than those expected to cause such dysrythmias. Therefore a device delivering NCAP can safely be applied to either the right or left vagus.

We have also found, surprisingly, that the Therapy Window is maximized on the cervical vagus through the use of a bipolar cuff electrode design. Key parameters of the cuff may be: spacing and shielding of the contacts. For example, the contact points or bands may be spaced 1-2 diameters of the vagus nerve apart, and it may be helpful to shield current from these contacts from other nearby structures susceptible to inadvertent triggering. The cuff may be further optimized by using bands which are as long and wide as possible to reduce neurostimulator power requirements.

Figure 3A:
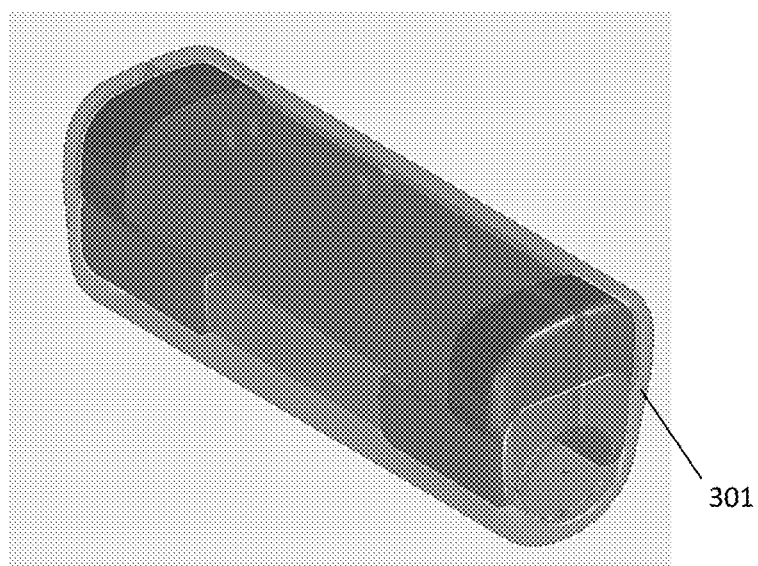
FIG. 3A shows one variation of a microstimulator in a POD configured to surround a nerve of the inflammatory reflex.
Figure 3B:
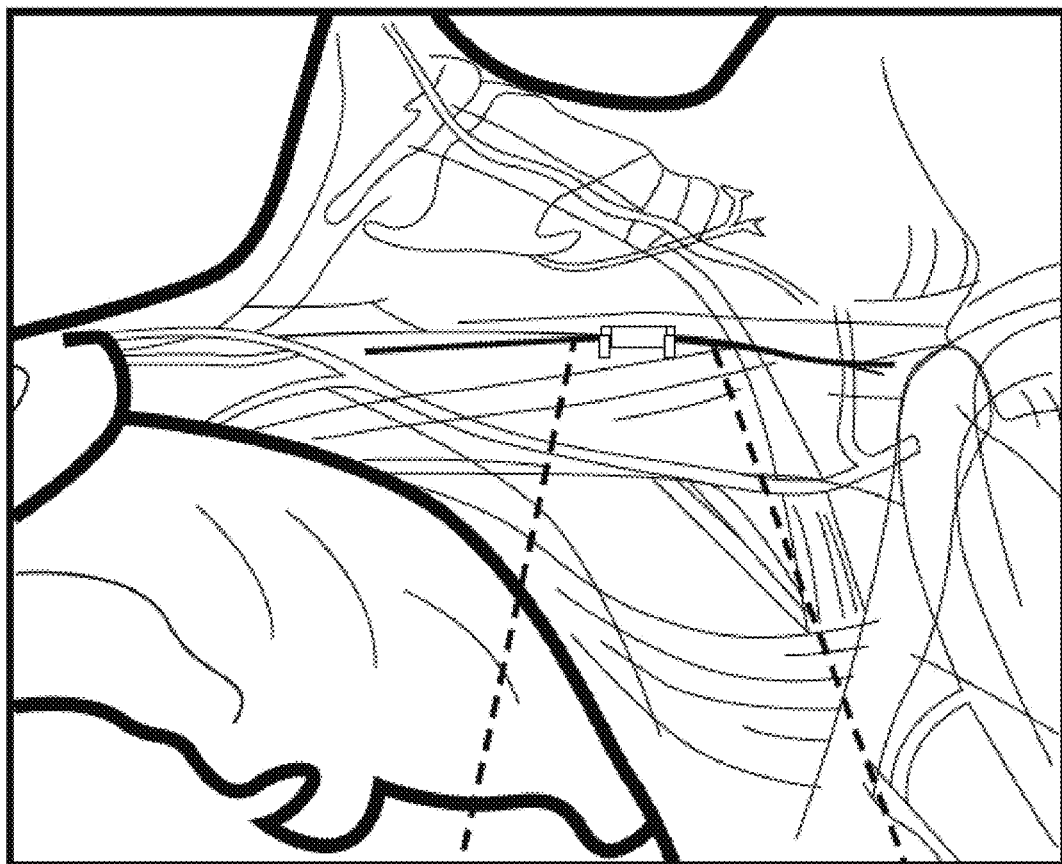
FIG. 3B shows an enlarged view of the microstimulator and POD.
Figure 3B:
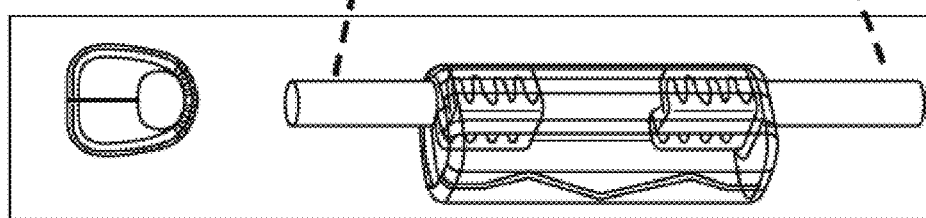
Figure 3C:
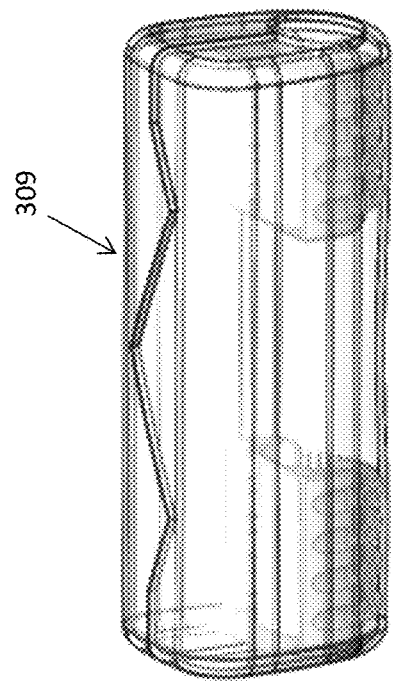
FIG. 3C shows another variation of a microstimulator.
Figure 3D:
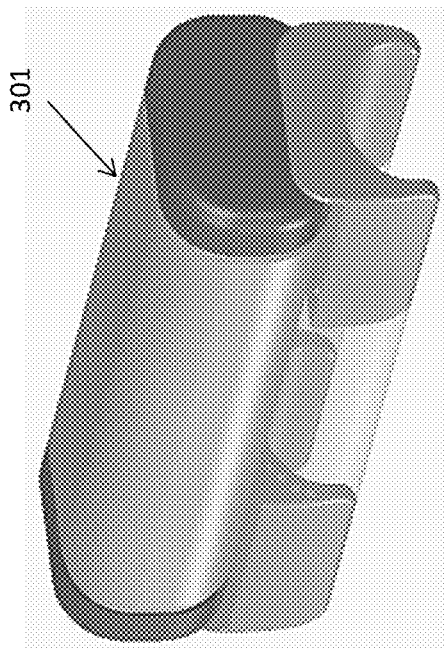
FIG. 3D shows the microstimulator of FIG. 3C within a POD.

Thus, any variations of the systems described herein (e.g., the NCAP system) may be implemented with a Cuff, Lead and Implantable Pulse Generation (IPG), or a Leadless Cuff. The preferred implementation is a leadless cuff implemented by a microstimulator with integral electrode contacts in intimate contact with the nerve and contained within a Protection and Orientation Device (POD). This is illustrated in FIGS. 3A and 3B. The POD 301 may form a current shield, hold the microstimulator into place against the vagus nerve, and extend the microstimulator integral contacts with integral contacts in the POD itself. The POD is typically a polymer shell that encapsulates a microstimulator implant and that allows a nerve to run through the interior against the shell wall parallel to the length of the microstimulator implant. Within the shell of the POD, the microstimulator implant remains fixed against the Vagus nerve so the electrodes remain in contact with the nerve. The POD anchors the implant in place and prevents the implant from rotating or separating from the nerve, as well as maintaining contact between the electrodes and the nerve and preserving the orientation as necessary for efficient external charging of the microstimulator battery.

The circuitry of any of the microstimulators described herein may include a motion detector (e.g., accelerometer or any other vibration sensor/detector, particularly those having low power requirements). In addition or alternatively, any of these apparatuses may include a microphone for detecting vibrations (including auscultation), a temperature sensor for detecting patient temperature (e.g., of nerve, body, blood, etc.), or the like. Although one or more additional electrical sensors (electrodes) may be used for detecting electrical potentials from the body, in some variations the same electrodes used to apply VNS may be configured to record electrical activity, and in particular the microstimulator may be configured to determine electrocardiogram (ECG) data, including heart rate and heart rate variability. In some variations the one or more sensors may be present on the microstimulator and/or the POD. Alternatively or additionally, the microstimulator may be configured to receive data regarding one or more metric from a sensor that is separate from the microstimulator, e.g., via the wireless radio (e.g., Bluetooth, etc.) within the microstimulator; this data may be analyzed and/or aggregated with other data for storage, transmission and/or analysis by the microstimulator, including in particular for modulation of the applied VNS.

Referring back to FIG. 1C, the system may include an implantable microstimulator contained in a POD, a Patient Charger, and a prescription pad that may be used by the clinician to set dosage parameters for the patient. This system may evaluate the efficacy, safety, and usability of an NCAP technology for chronic treatment of clinical patients. The system can employ a Prescription Pad (external controller) that may include the range of treatment options.

As described in more detail in U.S. patent application Ser. No. 12/874,171, titled "PRESCRIPTION PAD FOR TREATMENT OF INFLAMMATORY DISORDERS", filed on Mar. 3, 2011, Publication No. US-2011-0054569-A1, incorporated by reference in its entirety herein, the Prescription Pad may incorporate workflows in a simplified interface and provide data collection facilities that can be transferred to an external database utilizing commercially robust and compliant methods and procedures. In use, the system may be recommended for use by a clinician after assessing a patient; the clinician may determine that treatment of chronic inflammation is warranted. The clinician may then refer the patient to an interventional doctor to implant the microstimulator. Thereafter then clinician (or another clinician) may monitor the patient and adjust the device via a wireless programmer (e.g. prescription pad). The clinician may be trained in the diagnosis and treatment procedures for autoimmune and inflammatory disorders; the interventional placement of the system may be performed by a surgeon trained in the implantation of active neurostimulation devices, with a sufficient depth of knowledge and experience regarding cervical and vagal anatomy, experienced in performing surgical dissections in and around the carotid sheath.

Figure 1D:
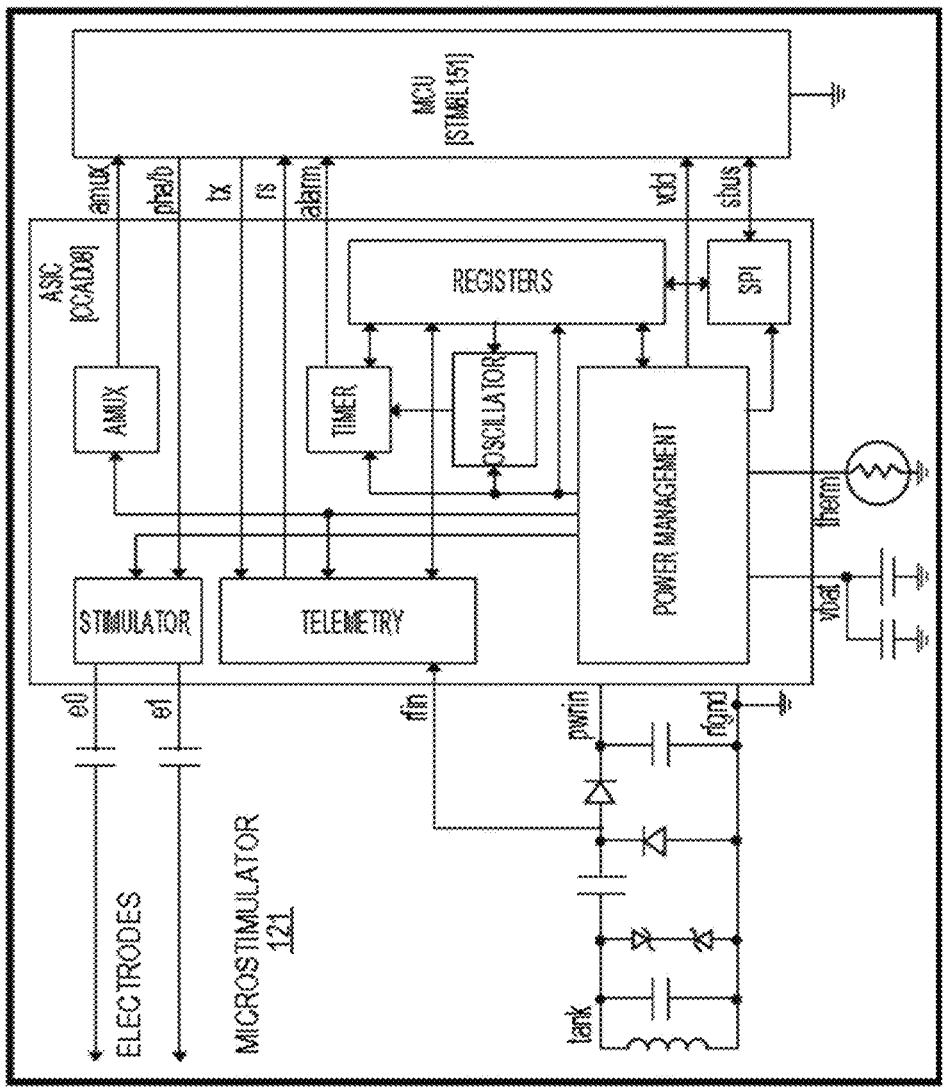
FIG. 1D is a block diagram schematically illustrating the microstimulator and the charger.
Figure 1D:
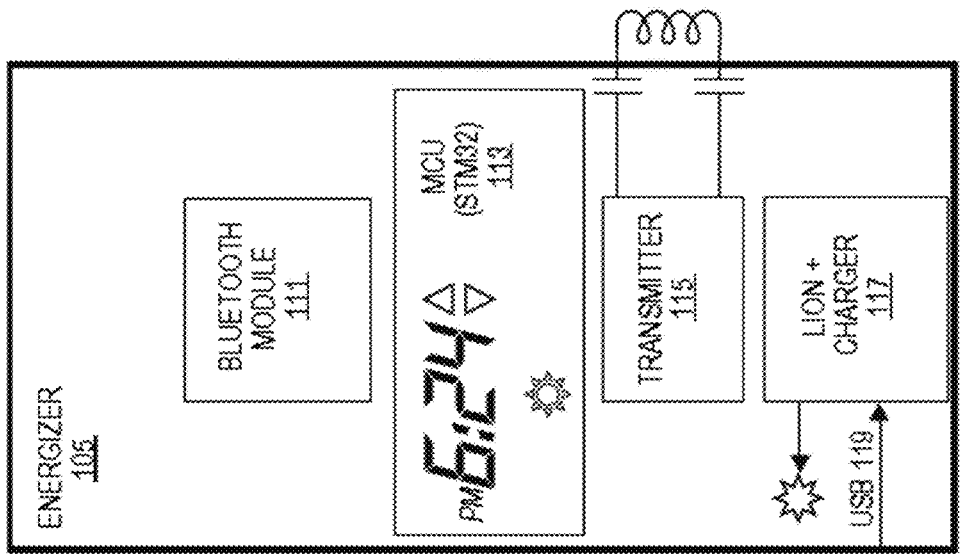

The system may output signals, including diagnostics, historical treatment schedules, or the like. The clinician may adjust the device during flares and/or during routine visits. Examples of implantation of the microstimulator were provided in U.S. patent application Ser. No. 12/874,171, titled "PRESCRIPTION PAD FOR TREATMENT OF INFLAM- MATORY DISORDERS", filed on Mar. 3, 2011, Publication No. US-2011-0054569-A1. For example, the implant may be inserted by making an incision in the skin (e.g., ≈3 cm) along Lange's crease between the Facial Vein and the Omohyoid muscle, reflecting the Sternocleidomastoid and gaining access to the carotid sheath. The IJV may be displaced, and the vagus may be dissected from the carotid wall (≤2 cm). A sizing tool may be used to measure the vagus, and an appropriate Microstimulator and POD Kit (small, medium, large) may be selected. The POD may then be inserted under nerve with the POD opening facing the surgeon, so that the microstimulator can be inserted inside POD so that the microstimulator contacts capture the vagus. The POD may then be sutured shut. In some variations a Surgical Tester may be used to activate the microstimulator and perform system integrity and impedance checks, and shut the microstimulator off, during or after the implantation. In other variations the surgical tester may be unnecessary, as described in greater detail below. A schematic of the internal components of the microstimulator and the charger can be seen in FIG. 1D.

A physician may use the Patient Charger to activate the microstimulator, perform integrity checks, and assure sufficient battery reserve exists. Electrodes may be conditioned with sub-threshold current and impedances may be measured. A Physician may charge the microstimulator. In some variations a separate charger (e.g., an "energizer") may be used by the patient directly, separate from the controller the physician may use. Alternatively, the patient controller may include controls for operation by a physician; the system may lock out non-physicians (e.g., those not having a key, code, or other security pass) from operating or modifying the controls.

In general, a physician may establish safe dosage levels. The physician may slowly increment current level to establish a maximum limit (Upper Comfort Limit). This current level may be used to set the Dosage Level. The exact procedure may be determined during this clinical phase.

The Physician may also specify dosing parameters that specify dosage levels and dosage intervals. The device may contain several concurrent dosing programs which may be used to acclimate the patient to stimulus, gradually increase dosage until efficacy is achieved, reset tachyphylaxis, or deal with unique patient situations.

Figure 2:
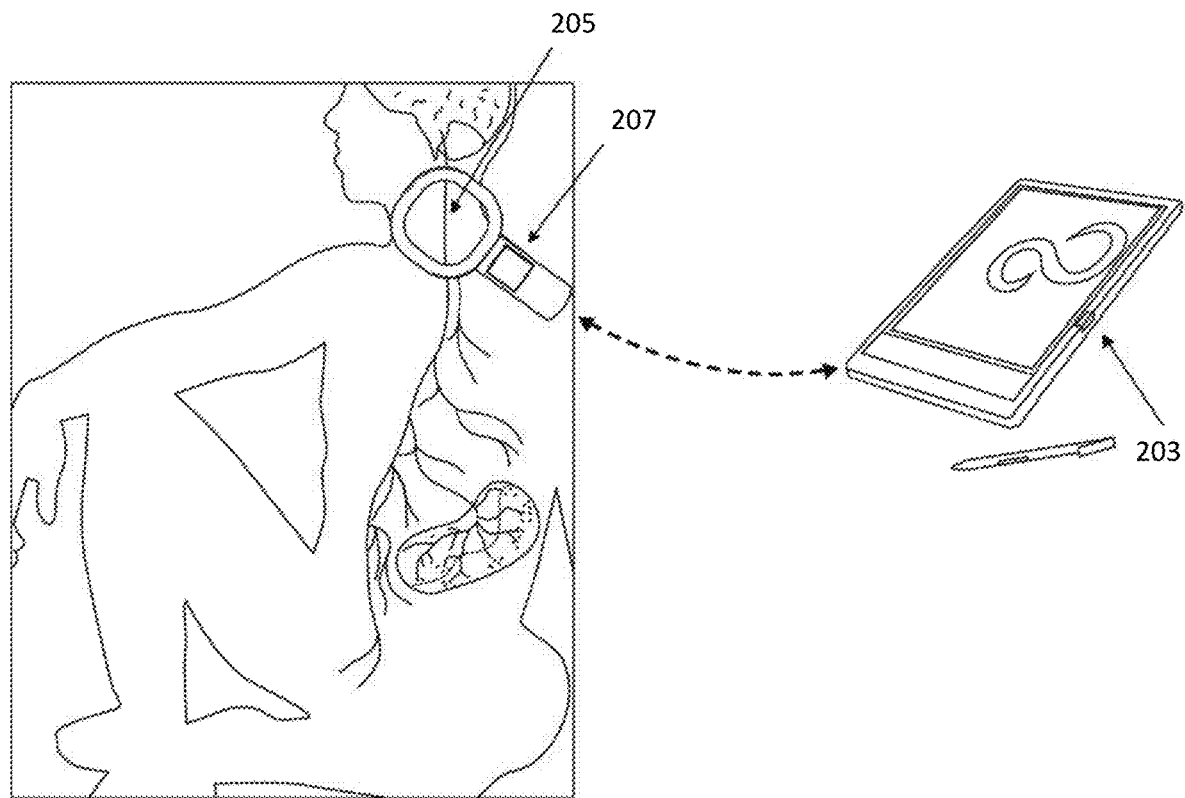
FIG. 2 illustrates one variation of an external system programmer/controller wirelessly connected to a microstimulator.

In some variations, the Prescription Pad may be configured to handle multiple patients and may index their data by the microstimulator Serial Number. For example, a Prescription Pad may handle up to 100,000 patients and 10,000 records per patient, and may store the data in its local memory and may be backed up on an external database. In some variations, during each charging session, accumulated even log contents will be uploaded to the Patient Charger for later transfer to Prescription Pad. The data may or may not be cleared from the microstimulator. For example, FIG. 2 shows the addition of a prescription pad 203 wirelessly connected to the charger/programmer 207.

The microstimulators described herein are configured for implantation and stimulation of the cholinergic anti-inflammatory pathway, and especially the vagus nerve. In particular the microstimulators described herein are configured for implantation in the cervical region of the vagus nerve to provide extremely low duty-cycle stimulation sufficient to modulate inflammation. These microstimulators may be adapted for this purpose by including one or more of the following characteristics, which are described in greater detail herein: the conductive capsule ends of the microstimulator may be routed to separate electrodes; the conductive capsule ends may be made from resistive titanium alloy to reduce magnetic field absorption; the electrodes may be positioned in a polymer saddle; the device includes a suspension (e.g., components may be suspended by metal clips) to safeguard the electronics from mechanical forces and shock; the device may include an H-bridge current source with capacitor isolation on both leads; the device may include a built in temperature sensor that stops energy absorption from any RF source by detuning the resonator; the device may include a built-in overvoltage sensor to stop energy absorption from any RF source by detuning resonator; the system may include DACs that are used to calibrate silicon for battery charging and protection; the system may include DACs that are used to calibrate silicon for precision timing rather than relying on crystal oscillator; the system may include a load stabilizer that maintains constant load so that inductive system can communicate efficiently; the system may include current limiters to prevent a current rush so that the microstimulator will power up smoothly from resonator power source; the system may extract a clock from carrier OR from internal clock; the device may use an ultra-low power accurate RC oscillator that uses stable temperature in body, DAC calibration, and clock adjustment during charging process; the device may use a solid state UPON battery that allows fast recharge, supports many cycles, cannot explode, and is easy to charge with constant voltage; and the device may include a resonator that uses low frequency material designed not to absorb energy by high frequency sources such as MRI and Diathermy devices.

Many of these improvements permit the device to have an extremely small footprint and power consumption, while still effectively modulating the vagus nerve.

FIG. 3A is a perspective drawing of the Pod containing the microstimulator. Sutures (not shown) are intended to be bridged across one to three sets of holes. Electrodes integrated into the pod are not shown but would extend as bands originating and ending on the two outer pairs of suture holes.

Figure 3E:
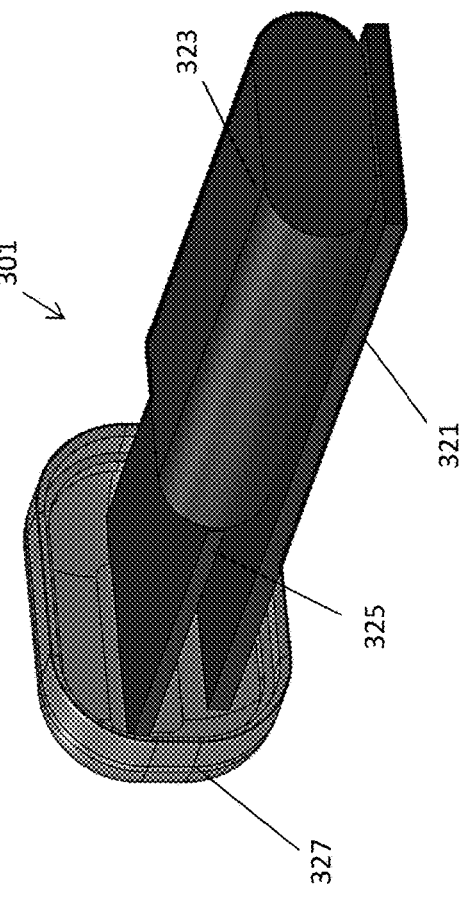
FIG. 3E shows another variation of the microstimulator.

In some variations, including those described above, the microstimulator consists of a ceramic body with hermetically sealed titanium-niobium ends and integral platinum-iridium electrodes attached. The microstimulator may be designed to fit within a POD 309, as shown in FIGS. 3A-3D. As described above, the POD is a biocompatible polymer with integrated electrodes that may help the microstimulator to function as a leadless cuff electrode. In some variations, such as the variation shown in FIG. 3E, contained within the hermetic space of the microstimulator 301 is an electronic assembly that contains a rechargeable battery 321, solenoid antenna 323, hybrid circuit 325 and electrode contacts (Ti Alloy braze ring and end cap) 327 at each end to make contact with the titanium/platinum case ends.

Figure 4:
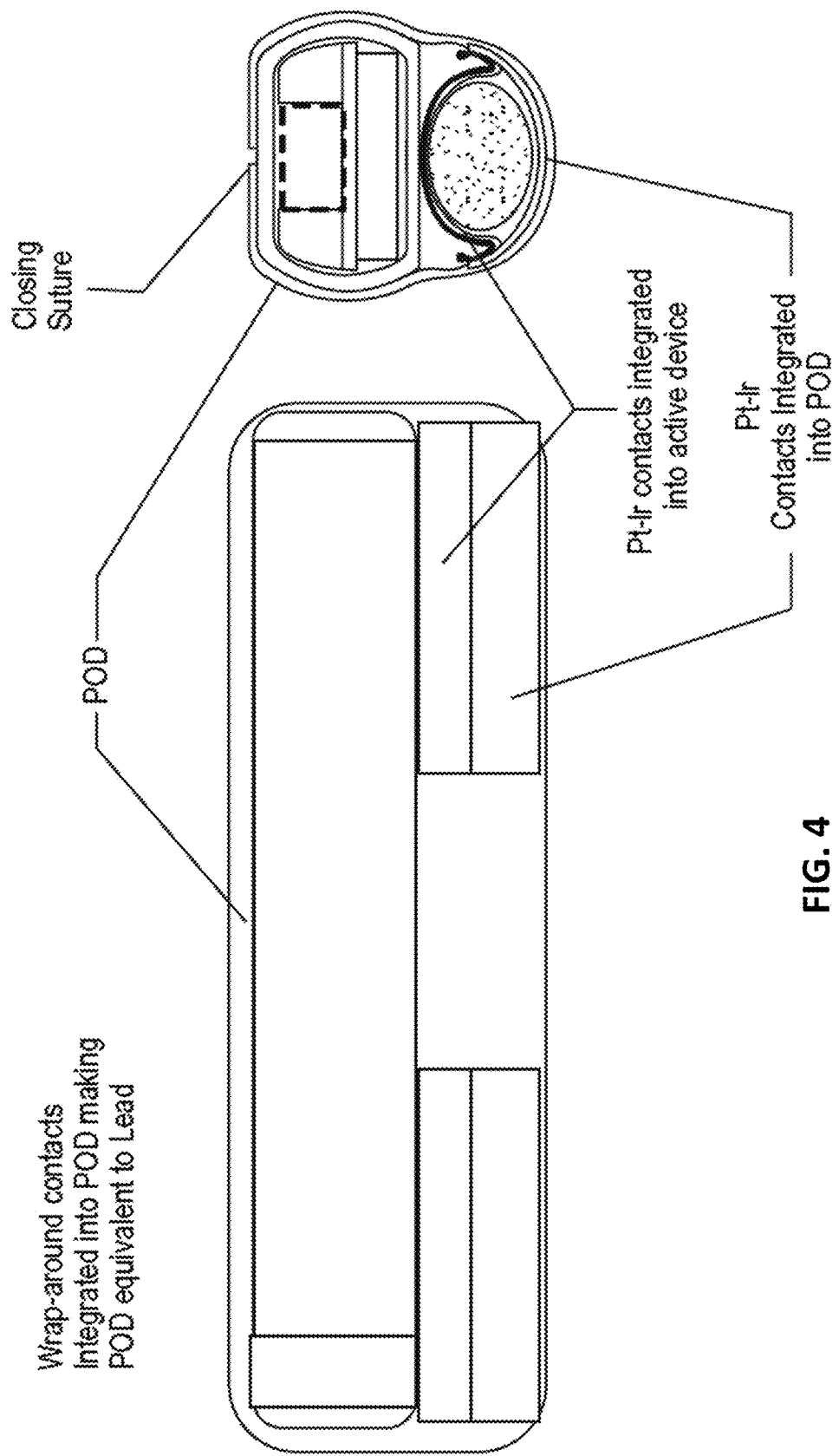
FIG. 4 shows a schematic diagram of a microstimulator and POD around vagus nerve.

As mentioned above, some of the device variations described herein may be used with a POD to secure the implant (e.g., the leadless/wireless microstimulator implant) in position within the cervical region of the vagus nerve so that the device may be programmed and recharged by the charger/programmer (e.g., "energizer"). For example, FIG. 4 shows a schematic diagram of a POD containing a microstimulator. The cross section in FIG. 4 shows the ceramic tube containing electronic assembly that includes the hybrid, battery and coil. The rigid or semi-rigid contacts are mounted on the tube and surround the oval vagus nerve. The POD surrounds the entire device and includes a metal conductor that makes electrical contact with the microstimulator contacts and electrically surrounds the nerve.

In some variations, the microstimulator may have a bipolar stimulation current source that produce as stimulation dose with the characteristics shown in table 1, below. In some variation, the system may be configured to allow adjustment of the "Advanced Parameters" listed below; in some variations the parameters may be configured so that they are predetermined or pre-set. In some variations, the Advanced Parameters are not adjustable (or shown) to the clinician. All parameters listed in Table 1 are ±5% unless specified otherwise.

TABLE 1

Microstimulator parameters

| Property | Value | Default |
|---|---|---|
| Dosage Amplitude (DA) | 0-5,000 µA in 25 µA steps | 0 |
| Intervals | Minute, Hour, Day, Week, Month | Day |
| Number of Doses per Interval | N = 60 Maximum | 1 |
| Advanced Parameters | | |
| Pulse width Range (PW) | 100-1,000 µS in 50 µS increments | 200 |
| Stimulus Duration (SD) | 0.5-1000 seconds per dose | 60 |
| Pulse Frequency (PF) | 1-50 Hz | 10 |
| Stimulus Voltage (SV) | ±3.3 or ±5.5 ±1 Volts | Automatically set by software |
| Constant Current Output | ±15% over supported range of load impedances (200-2000Ω) | |
| Specific Dose Time | Set a specific time between 12:00 am-12:00 am in one minute increments for each Dose Issue | Driven by default table (TBD) |
| Number of Sequential Dosing Programs | 4 maximum | 1 |

The Dosage Interval is defined as the time between Stimulation Doses. In some variations, to support more advanced dosing scenarios, up to four 'programs' can run sequentially. Each program has a start date and time and will run until the next program starts. Dosing may be suspended while the Prescription Pad is in Programming Mode. Dosing may typically continue as normal while charging. Programs may be loaded into one of four available slots and can be tested before they start running. Low, Typical, and High Dose schedules may be provided. A continuous application schedule may be available by charging every day, or at some other predetermined charging interval. For example, Table 2 illustrates exemplary properties for low, typical and high dose charging intervals:

TABLE 2 low typical and high dose charging intervals

| Property | Value |
|---|---|
| Low Dose Days Charge Interval | 30 days max: 250 µA, 200 µS, 60 s, 24 hr, 10 Hz, ±3.3 V |
| Typical Dose Charge Interval | 30 days max: 1,000 µA, 200 µS, 120 s, 24 hr, 10 Hz, ±3.3 V |
| High Dose Charge Interval | 3.5 days max: 5,000 µA, 500 µS, 240 s, 24 hr, 20 Hz, ±5.5 V, |

The system may also be configured to limit the leakage and maximum and minimum charge densities, to protect the patient, as shown in Table 3:

TABLE 3 safety parameters

| Property | Value |
|---|---|
| Hardware DC Leakage Protection | <50 nA |
| Maximum Charge Density | 30 µC/cm$^2$/phase |
| Maximum Current Density | 30 mA/cm$^2$ |

In some variations, the system may also be configured to allow the following functions (listed in Table 4, below):

TABLE 4

Additional functions of the microstimulator and/or controller(s)

| Function | Details |
|---|---|
| Charging | Replenish Battery |
| Battery Check | Determine charge level |
| System Check | Self Diagnostics |
| Relative Temperature | Temperature difference from baseline |
| Program Management | Read/Write/Modify a dosage parameter programs |
| Program Up/Download | Transfer entire dosage parameter programs |
| Electrode Impedances | Bipolar Impedance (Complex) |
| Signal Strength | Strength of the charging signal to assist the patient in aligning the external Charge to the implanted Microstimulator. |
| Patient Parameters | Patient Information |
| Patient History | Limited programming and exception data |
| Implant Time/Zone | GMT + Time zone, 1 minute resolution, updated by Charger each charge session |
| Firmware Reload | Boot loader allows complete firmware reload |
| Emergency Stop | Disable dosing programs and complete power down system until Prescription Pad connected |

As mentioned, one or more metrics (e.g., biomarkers, physiological parameters, etc.) may be measured including measured by the microstimulator and the microstimulator may be both adapted to measure the one or more metrics and/or to modulate the applied VNS based on the measured and/or analyzed metric(s).

For example, described herein are methods and apparatuses for detecting or measuring regulatory T cells (Tregs) and/or memory regulatory T cells (mTregs) either or both to provide a method of screening a patient's sensitive to VNS and/or for modulating the inflammatory response based on modulation of the VNS applied specific to that patient. Tregs are T-cells that are involved in maintaining tolerance to self-antigens, and more generally, the suppression of the immune response. One way Tregs achieve their function is by the suppression or down regulation of the induction and/or proliferation of effector T-cells.

Tregs can be characterized broadly into two groups, naïve Tregs (nTregs), which are CD4+CD25+CD127lowCD45RA+, and memory Tregs (mTregs), which are CD4+CD25+CD127lowCD45RO+. nTregs are precursors to mTregs that have not yet been exposed to their cognate antigen(s). Once nTregs have been exposed to their cognate antigen(s), they can become activated and may further develop into mTregs. mTregs can suppress and/or down regulate the immune response, including the inflammatory response, by secreting various suppressive cytokines and molecules that act on effector T cells and dendritic cells, such as IL-35, IL-10, and/or TGFβ, by metabolic disruption, and/or by inducing cytolysis of effector T cells and dendritic cells.

Furthermore, Treg cells have been found to have phenotypically and functionally heterogeneous populations, where specific subsets of Treg cells need different factors for their differentiation, maintenance, and also function in different inflammatory contexts and tissue. Treg cells can be divided into functionally distinct effector populations based on differential expression of adhesion and chemattractant receptors, those that target lymphoid tissue versus those that target non-lymphoid tissue to prevent inflammatory disease and maintain normal immune homeostasis. Treg cells have been found in a different tissue throughout the body including skin, intestine, lungs, liver, adipose, and skeletal muscle. Because Treg cells are recruited to inflamed tissue (sites) where they function to mitigate autoimmunity, and prevent collateral tissue damage during ongoing inflammation, control of Treg cells may be particularly useful in controlling autoimmune disease and tissue or organ transplanting procedures.

Memory Treg cells, as the name suggests, possess "memory" for encounters with a specific antigen. It has been found that after exposure to a particular antigen, the antigen-specific Treg cells become activated and recruited to the target tissue. After resolving the primary infection/inflammation, these activated Treg cells reside in the tissue even after the termination of the infection and in the absence of antigen. Upon re-encounter of the same antigen these Treg cells, now termed memory Treg cells, suppress a secondary inflammatory response and do so more efficiently than during the initial exposure to that antigen.

Previously disclosed methods have used implantable microstimulator on the Vagus nerve (VNS) to target inflammation. Experiments have shown that VNS can significantly inhibit disease severity by reducing the amount of inflammation and resulting damage. Surprisingly, it was also found that in some subjects treated, the application of VNS also increased the amount of memory Treg cells over a statistically significant amount. The increase in memory Treg cells is surprising because the application of VNS has an inflammation-reducing effect and Treg cells typically are activated and recruited in response to inflammation. Thus, one would expect Treg cell concentrations to decrease, and certainly not increase over the duration of VNS application where there is measureable decrease in overall inflammation. The increase in memory Treg cells in some subjects over the course of the VNS treatment was unexpected.

It would advantageous to harness both the beneficial effects of VNS and the increased presence of Treg cells in those suffering from diseases that cause inflammation, and autoimmune diseases that cause inflammation (such as rheumatoid arthritis).

Described herein are systems and methods of using VNS to modulate mTreg, using the concentration of mTreg to screen for "mTreg" responders to VNS, and using mTreg to set therapeutic dosing parameters for VNS to further decrease inflammatory response within these subjects.

VNS surprisingly resulted in an increase in nTregs and mTregs in some patients, while in other patients VNS fails to significantly increase Tregs; the results are shown in FIGS. 5A-9B. To generate the data shown in FIGS. 5A-9B, subjects suffering from rheumatoid arthritis were stimulated once at day 0 and 7, and once a day after day 7. At day 28, non-responders received 4 stimulations per day while responders continued to receive one stimulation per day. Subjects were characterized as responders or non-responders based on a change in their Disease Activity Score (DAS) scores and/or by using the American College of Rheumatology/European League Against Rheumatism (ACR/EULAR) response criteria, which categorizes patients as showing no, moderate, or good response. Subjects with a less than 20% change in their DAS scores were characterized as non-responders, while subjects with greater than 20% change were characterized as responders. The primary endpoint was determined at day 42 but measurements continued to day 84.

Figures 5A, 5B:
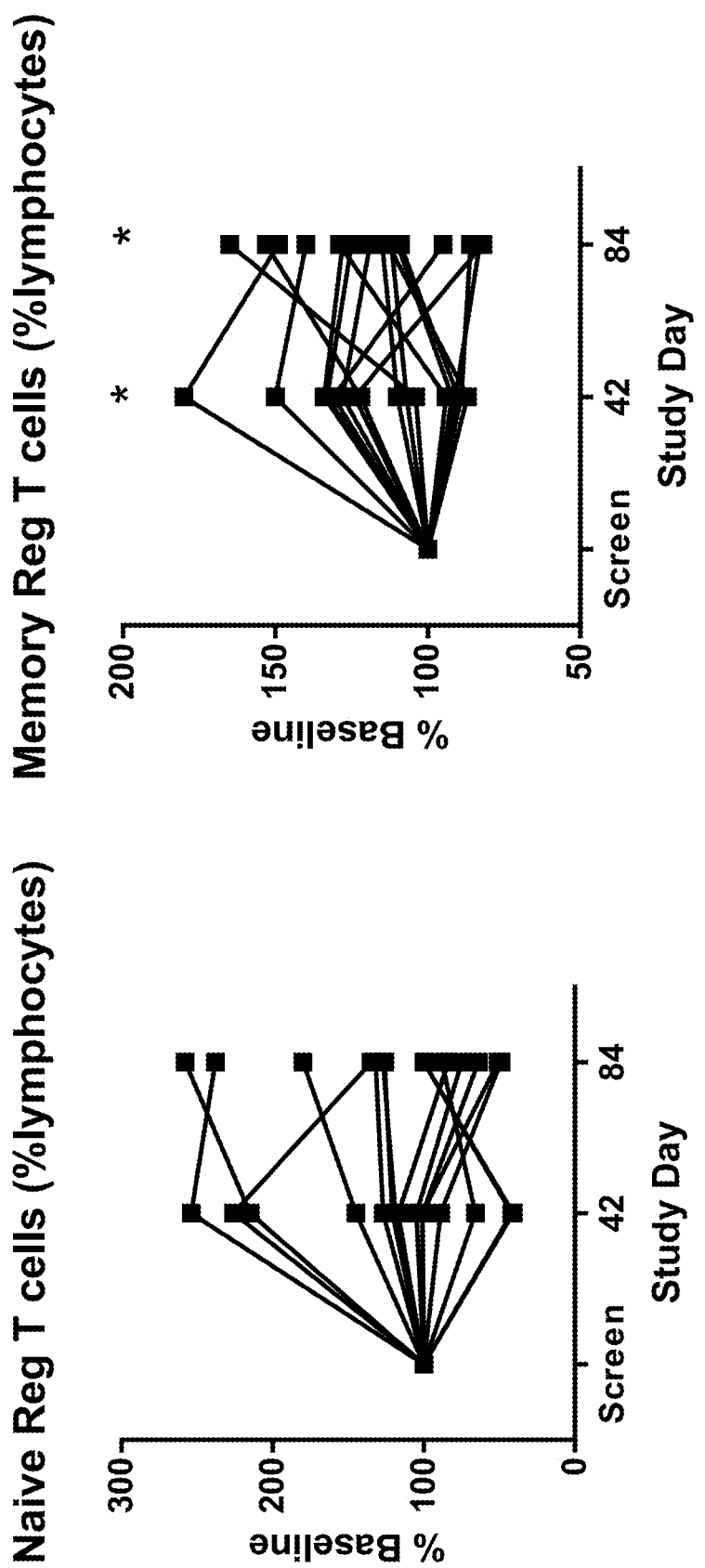
FIGS. 5A and 5B show the response of naïve regulatory T cells and memory regulatory T cells to vagus nerve stimulation.

FIGS. 5A and 5B show the response of naïve regulatory T cells and memory regulatory T cells to vagus nerve stimulation. This data shows a significant increase in memory T regulatory cells by paired ANOVA (across all subjects). The Y-axis shows the % baseline of nTregs (naïve regulatory T cells) or mTregs (memory regulatory T cells), where the baseline for each patient is determined at day zero (screen day) by calculating the ratio of nTregs or mTregs to the total number of lymphocytes. FIGS. 5A and 5B show that in some patients, VNS can increase the number of nTregs and/or mTregs, while other patients did not show a significant increase.

Figures 6A, 6B:
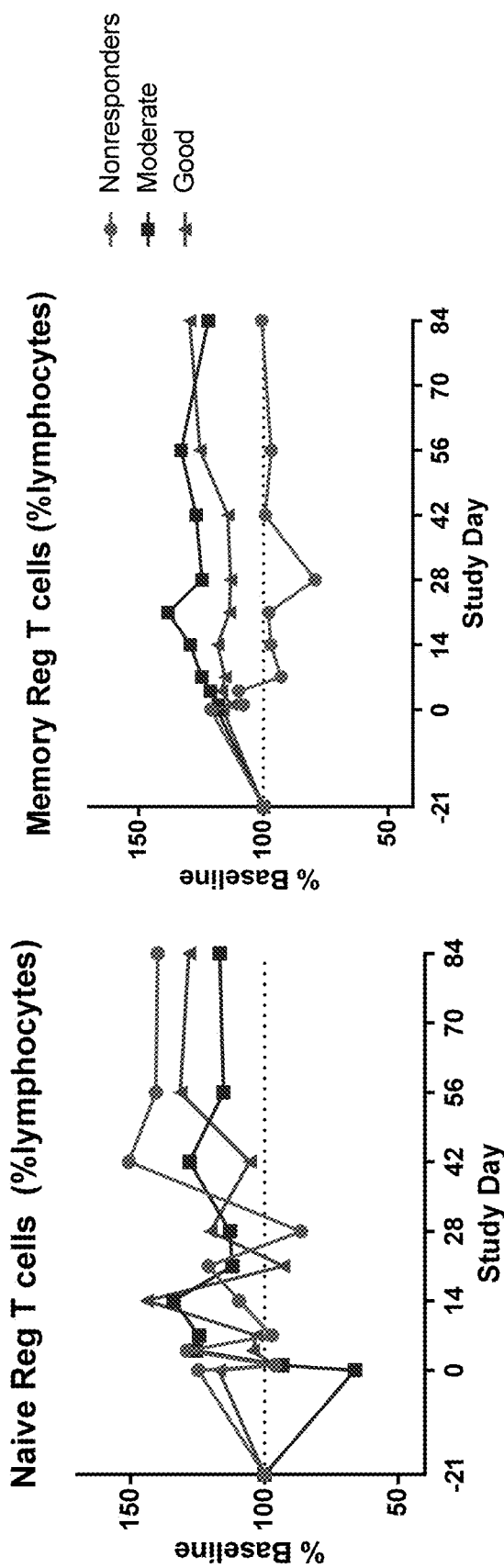
FIGS. 6A and 6B show the response of naïve regulatory T cells and memory regulatory T cells to vagus nerve stimulation in responders and non-responders.

FIGS. 6A and 6B show the response of naïve regulatory T cells and memory regulatory T cells to vagus nerve stimulation in responders and non-responders, and shows an increase in memory T regulatory cells in responders but not in non-responders. FIG. 6A shows a fairly random pattern of % lymphocytes associated with the Naïve Treg cells for the non-responder, moderate responder, and good responder populations. In contrast, FIG. 6B shows that responders in both the Moderate and Good categories had an increase in mTregs, while non-responders did not show an increase in mTregs. In both the Moderate and the Good responder groups, the increase in mTreg cells continued to be above pre-stimulation level even after the 28' day, while the non-responder group showed a short period of increase in % lymphocytes for mTreg cell before dropping to baseline throughout the remainder of the study.

Figure 6C:
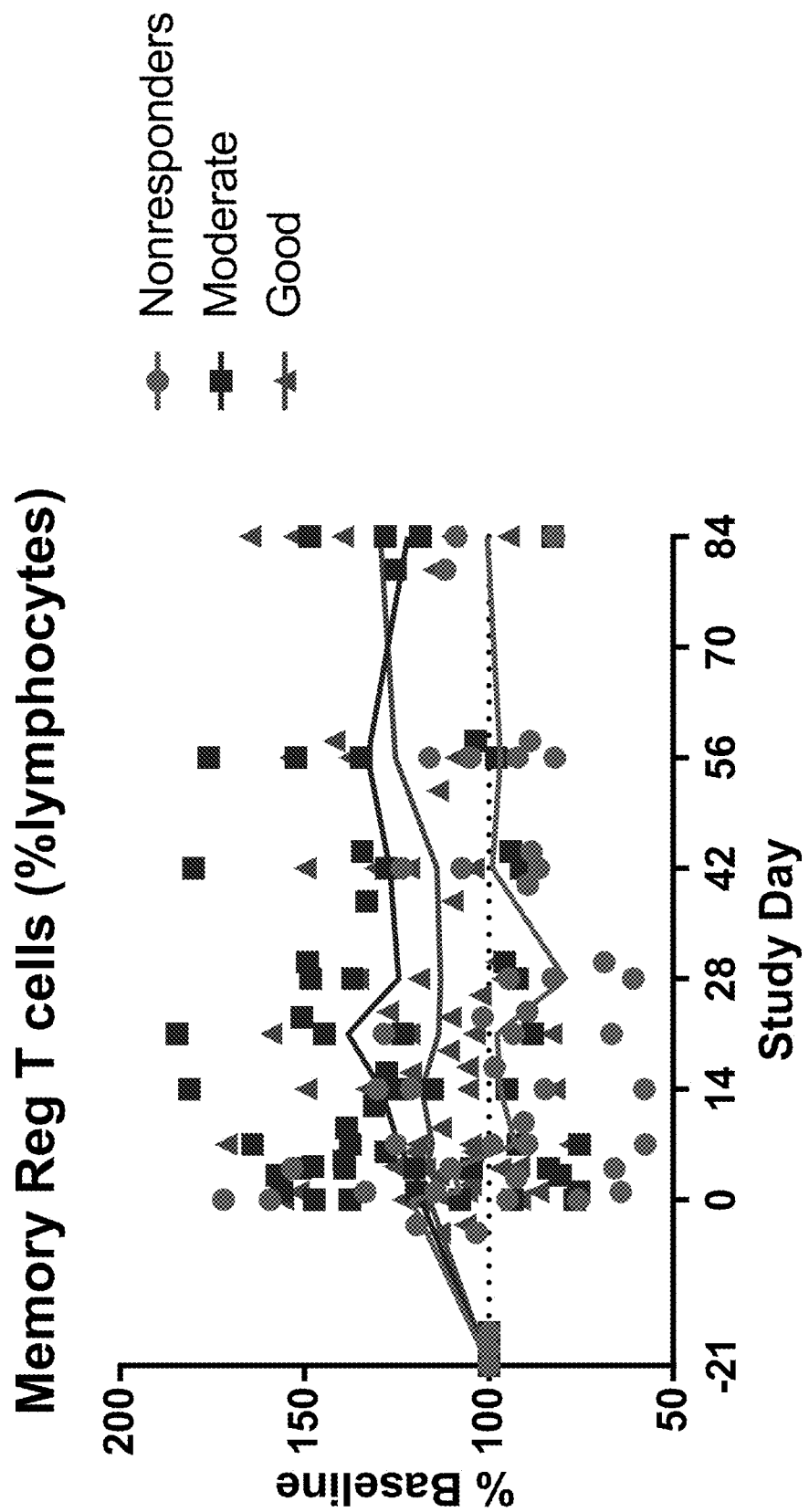
FIG. 6C shows raw data for non-responders, moderate responders, and good responders.
Figures 7A, 7B:
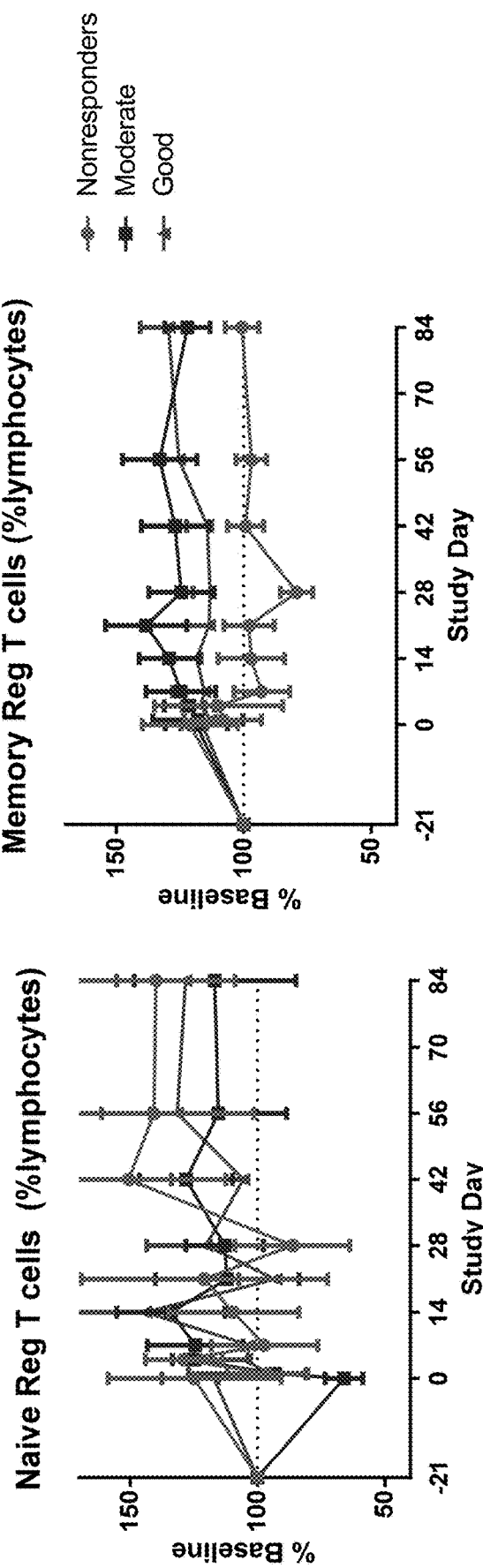
FIGS. 7A and 7B show a comparison of the increase in nTreg and mTreg in non-responders, moderate responders, and good responders.

FIG. 6C is a plot of the combined raw data of % lymphocytes for all subjects, while FIGS. 7A and 7B show the standard deviations of the previously shown data from FIGS. 6A and 6B. In particular, it can be seen that the results seen for % lymphocytes in mTreg cells is statistically significant for all three groups recorded.

Figure 8A:
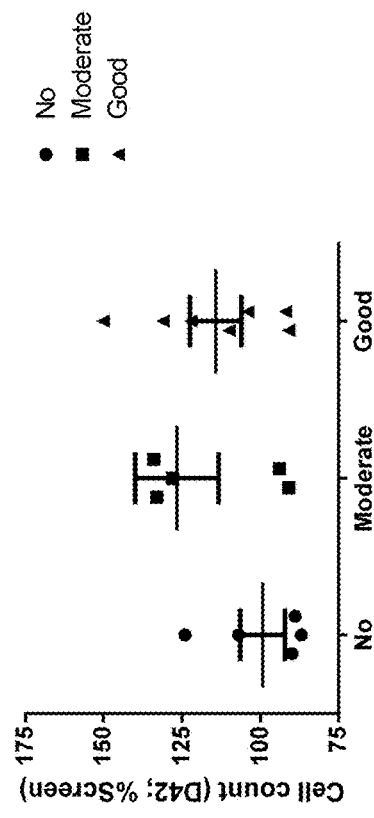
Figure 8C:
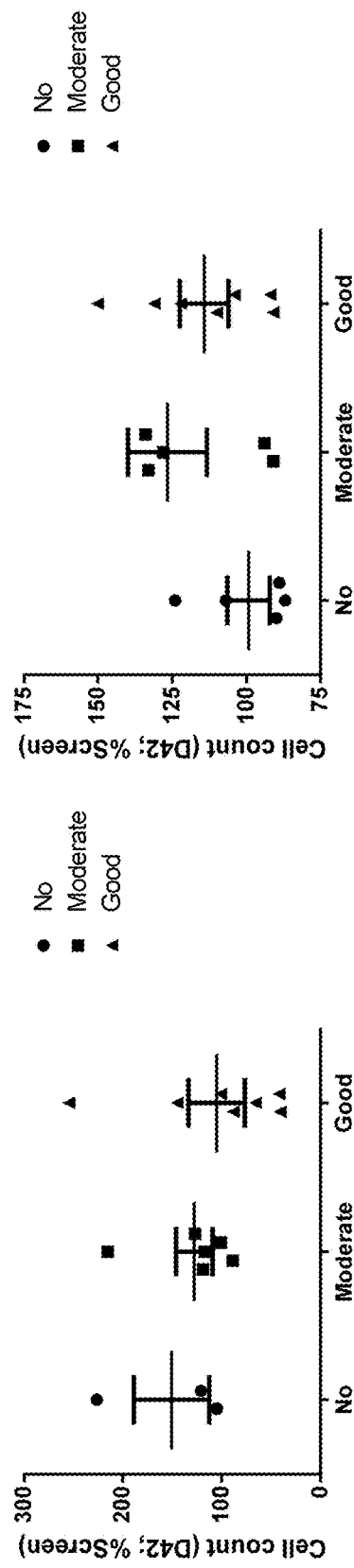
Figure 8B:
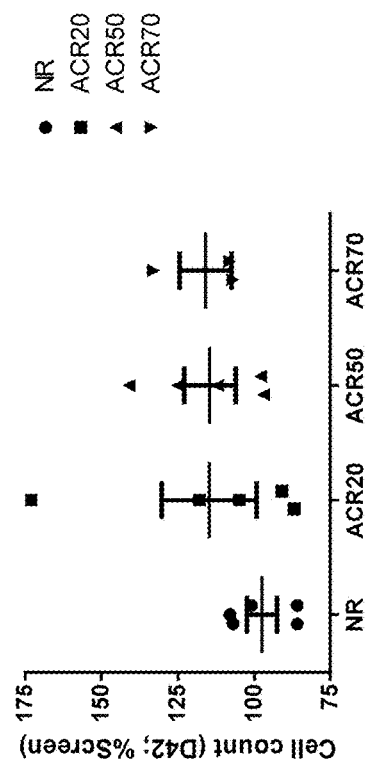
Figure 8D:
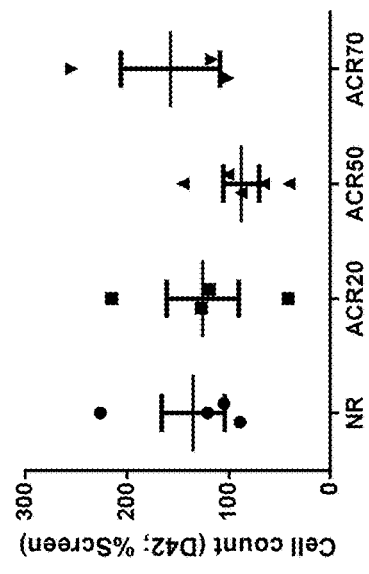

Turning to FIGS. 8A-8F, these figures show the response of naïve regulatory T cells and memory regulatory T cells to vagus nerve stimulation in good responders, moderate responders, and non-responders, where the categories of responders are further broken down into various degrees of r [EULAR score]. The measure of inflammation is qualitative. One can easily see that for the nTreg cell population sampled, there tended to be no significant correlation between cell count and the three different groups of subjects (non-responders, moderate responders, and good responders) (FIG. 8A). Further, the ACR scores for each group of subjects (non-responders, moderate responders, and good responders) did not correlate well with respect to the nTreg cells (FIG. 8B). FIGS. 8C and 8D show the cell count and ACR values for mTreg cells correlate well with the non-responder group, the moderate response group and the good responder group. There is also good correlation with the increase in the amount of mTreg and the increase in ACR scores from the three group of subjects.

Figures 9A, 9B:
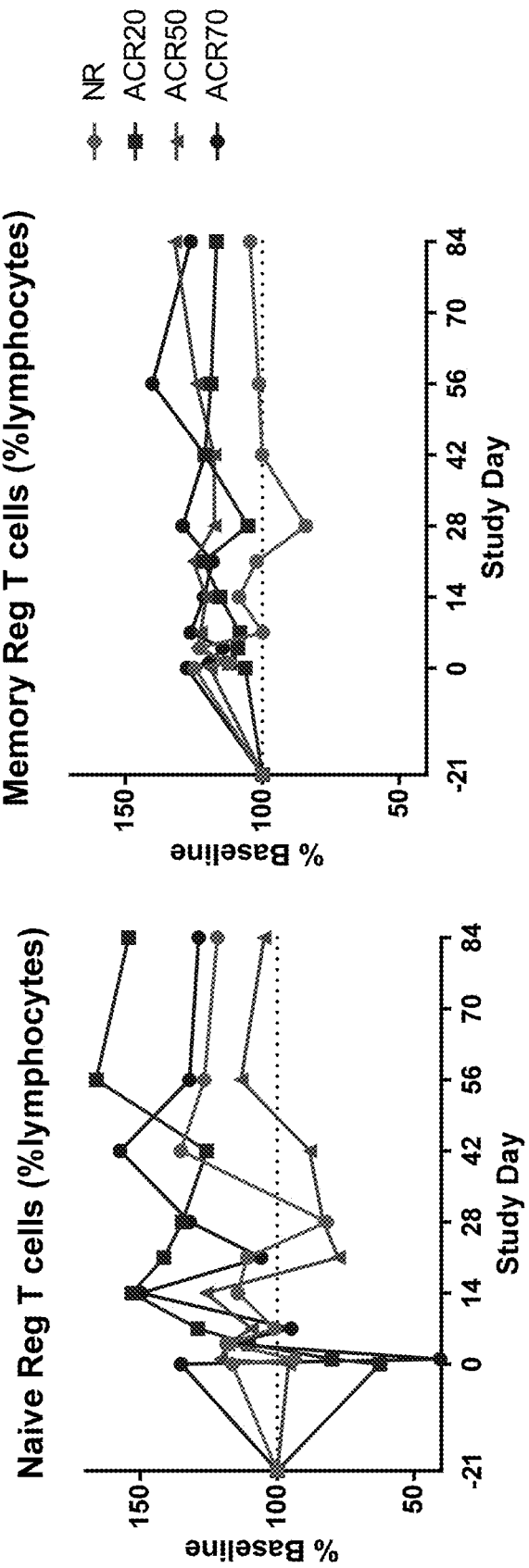
FIGS. 9A and 9B show a comparison between percentage increase of nTreg compared to mTregs as a function of study days for non-responders, and for those that reported ACR scores of ACR20, ACR50, and ACR70 respectively.

Finally, turning to FIGS. 9A and 9B, where these graphs show the percent increase in the cell type (naïve Treg shown in FIG. 9A and memory Treg shown in FIG. 9B) over the study period as it might correlate to different ACR scores reported. As can be seen from FIG. 9A, there does not appear to be a correlation between the different ACR scores that subjects reported as it relates to the percent cell for the naïve Treg cells. FIG. 9B however shows a general tendency for the subjects that reported greater improvements (ACR50 and ACR70) to be two highest plotted lines, with the trace for non-responders hovering around baseline, and ACR20 being in in the middle. Therefore, the data shows that responders to VNS were correlated with an increased percentage of memory Treg cells, while non-responders did not show any increase in the percentage of memory Treg cells.

In all the data described above, some subjects possessed T regulatory cells, and particularly memory T regulatory cells, that showed moderate to good response to stimulation application, while others possessed T regulatory cells that did not respond to stimulation in any significant way. It would be preferable to determine whether a subject's T regulatory cells, and particularly memory T regulatory cells, are responsive to stimulation prior to implanting the stimulation device around their vagus nerve. Thus, less invasive screening methods may be implemented to determine whether a subject's Treg cells are responsive to stimulation. In such preliminary test, qualitative evaluation of improvements on inflammation may also be assessed. In both preliminary assessments, it is understood that the external stimulation may only have a fraction of the beneficial effects compared to when the stimulation is directly applied to the vagus nerve.

Preliminary testing of Treg cell response to stimulation within subjects may be performed in a minimally-invasive or non-invasive manner. Non-invasive stimulation described herein is non-invasive mechanical stimulation applied at a predetermined range of intensities, frequencies, and duty-cycles. Also, non-invasive electrical stimulation may also be applied. For example, non-invasive stimulation may be through couplers in communication with an actuator that may be part of a stimulation device that is configured to stimulate at least a portion of the subject's ear. In other examples, mechanical actuators or electrical stimulation leads, electrodes, clips, or couplers that allow for stimulation of the peripheral branches of the vagus nerve may be used. In some embodiments, the electrical stimulation can be delivered through the skin to the vagus nerve using a transcutaneous electrical nerve stimulation (TENS) device. The TENS device can be place over any portion of the body which is in proximity to the vagus nerve or one of its branch nerves, such as the ear or neck.

In other embodiments, the minimally invasive electrical stimulation used in the screening test can be delivered directly to the nerve using a needle electrode.

More specifically, mechanical stimulation may be applied to a subject's ear, in particular, the cymba conchae region. Mechanicals stimulation may also be applied to other appropriate regions of the subject's body. In some examples, the non-invasive stimulation may be mechanical stimulation between about 50-500 Hz and having appropriate duration (e.g. less than 5 minutes, less than 3 minutes, less than 1 minute, and so forth), at an appropriate intensity and frequency.

In other examples, preliminary testing may include electrical stimulation applied to the pinna. The pinna region of the ear has little or no hair and several cranial and cervical spinal nerves project to this portion of the ear. Other regions targeted may include vagal nerve endings in the conch of the ear. In some examples, the electrical stimulation may be with frequencies as described herein and, for example, peak intensity of up to 2, 5, 10, 15, or 20 mA. The electrical stimulation may occur every few hours and where the electrical stimulation uses the parameters described herein except that the intensity of the stimulation may be increased up to 2, 5, 10, 15 or 20 mA in order to penetrate through the skin and other tissues to reach the nerve.

The effect of stimulation on the concentration of Treg cells may then be studied. A baseline level of T regulatory cells may first be determined by measuring the amount of T regulatory cells in the subject's blood before stimulation is applied. This may be done with known analytical techniques such as flow cytometry. Other methods of arriving at the concentration of T regulatory cells may be through determining the concentration of associated gene segments and markers within the DNA or RNA of the Treg cells. This may include using known methods for assaying the FOXP3 gene which is centrally involved in the development and function of the Treg cells. Yet another method for determining the concentration of Treg cells may involve challenge with a particular antigen having a known concentration. Once baselines have been taken for a subject, non-invasive or minimally-invasive stimulation may be applied over a given length of time, with a particular frequency, and over a course of time. Changes in Treg cell concentrations, particularly mTreg cell concentrations can be mapped to the application of stimulus. Memory T-regulatory cells can be identified as CD4+CD25+CD127LowCD45RO+ using various techniques and/or can be identified by its expression of the FOXP3 gene. Naïve T-regulatory cells can be identified as CD4+CD25+CD127lowCD45RA+.

Cutoffs may be set for determining whether a subject is responding positively to the stimulation. The cutoffs may be either quantitative (increase in mTreg cells), qualitative (a subject's evaluation of improvement in their inflammation based on EULAR or ACR scoring), or a combination of both. For example, a threshold limit of 20 percent Treg cells above baseline may be correlated to having a positive effect. In other examples, the threshold limit may be set at 10 percent, 30 percent, 40 percent, or 50 percent above baseline to indicate a positive response. It should also be noted that the percent above baseline limit set may also be an average value. Having an average value above baseline will reveal where data is extremely noisy and does not in fact show any positive response even though a few values are above the set threshold.

In some instances, stimulation amplitude, frequency (as in the number of stimulations applied per day), or the "on" period for the stimulation may be step-wise increased or ramped up to determine, for example, if increasing the amplitude or length of time according to Table 1 results in an increase in memory T-regulatory cells. For example, the parameters listed in Table 1 may be adjusted to determine whether altering these parameters might have a measureable effect on the concentration of mTreg cells and/or the level of inflammation experienced by the subject. In some embodiments, one or more parameters can be adjusted until the level of mTreg cells increases by a predetermined amount, such as 10, 20, 30, 40, or 50 percent above a baseline level measured before stimulation. This can be used to set the dosing of an implanted microstimulator.

In implementation, the concentration of memory cells (e.g., mTreg, nTreg or both) may be determined external to an implant and the data provided to the implant, as mentioned (e.g., by flow cytometry). Alternatively, the implant may be configured to measure or detect the level of memory cells or changes in the level(s) of memory cells. For example, the implant may include a microfluidics detector for receiving and analyzing blood, including memory T cells, and/or an immunofluorescence detection/quantification of memory T-cells.

As mentioned above, alternatively or additionally, and other metric, including but not limited to heart rate and heart rate variability may be used as a screen and/or to adjust VNS. Thus, a body and/or wellness sensor may be used to modulate the activity of an implanted neurostimulator (microstimulator). These sensors may be integrated into the implant or they may be separate from the implant, including databases tracking wellness/fitness of the user unrelated to the implant. For example, motion tracking may be used. In some variations an accelerometer can be used to measure patient activity, which may be correlated with the level of inflammation suffered by the patient, and used to modulate one or more stimulation parameters, such as stimulation amplitude, stimulation duration, and the frequency of stimulations. In another example, heart rate and/or heart rate variability can be used to modulate one or more stimulation parameters. Any of the implants described herein may include such a sensor (e.g., accelerometer, etc.) and any of these systems may be adapted to use this sensor information to modulate the applied stimulation.

In some embodiments, one or more sensors can be used to measure various metrics (e.g., physiological parameters such as HR, HRV, respiration rate, body temperature, etc.), which can then be used to modulate vagus nerve stimulation (VNS). For example, a motion sensor (such as an accelerometer) can be used to measure patient activity. Alternatively or additionally, a core body temperature may be used to detect changes in body temperature indicative of disease states. Similarly, a sensor for detecting a particular analyte (e.g., a biomarker for inflammation, such as a cytokine and/or memory T cells, as just described) may be included. Alternatively or additionally, the implant may receive information (or a charger/controller coupled or coupleable to the implant) on the subject's physical parameters (e.g., heart rate, subjective/reported wellbeing, etc.) from an external database that may be used in a one-time or ongoing manner to adjust, increase, decrease, stop, start, or otherwise modify an applied treatment regime by the implant.

In particular, described herein are implants including at least a motion sensor such as an accelerometer. The accelerometer may be incorporated within the implant and/or the implant (or a controller affiliated with the implant) may receive information from a motion sensor (e.g., accelerometer) that is worn and/or implanted in the subject. For example, motion information or other wellbeing data from a wearable electronic device (e.g., Fitbit, etc.) may be provided to the implant and/or controller and used to modify one or more treatment parameter. Treatment parameters include dosing parameters such as frequency, amplitude, duty cycle, etc. as described above.

For example, in patients suffering from rheumatoid arthritis (RA), it has been observed that during flare-ups of RA, the patient typically exhibits less overall body motion, potentially due to pain in the joints. Therefore, a low amount of physical activity may indicate an increased need for treatment due to the presence of inflammation. Thus motion sensing may be used to increase/decrease applied therapy by the VNS (e.g., using a microstimulator as described herein).

If an accelerometer is included, it may be uniaxial, triaxial, or the like. As mentioned, the accelerometer can be located within the implant, or can be worn separately on another part of the body such as the arms, legs, torso, or wrist, for example. If the accelerometer is separate from the microstimulator, then the accelerometer can include wireless communications, such as Bluetooth, in order to transmit the data to the implant (microstimulator), and/or charger, and/or a prescription pad. In some embodiments, this data is transmitted to an external database, which may include data from a large population of patients. The transmitted data can include the stimulation parameters and protocol used and patient information and characteristics when the physical activity was measured. In some embodiments, a physical activity index can be generated for a patient. The index can be normalized to an activity level at time zero, or an activity level when the patient feels that the inflammation is well controlled, or an activity level when the patient feels that the inflammation is not being well controlled. In some embodiments, the physical activity index may be a combination of the patient's data and data from an external database that represents a compilation of the data from a larger patient population. In some embodiments, the physical activity index can be generated solely from the external database. In some embodiments, by comparing the measured activity level to the physical activity index, the system can determine whether the inflammation is getting better or worse or staying the same. In some embodiments, the data from the accelerometer can be used to generate a physical activity score. In some embodiments, the physical activity level can be correlated to the level of inflammation suffered by the patient. More generally, in some embodiments, the physical activity level can be used to determine a disease state. In other embodiments, the physical activity level can be used directly by itself without any correlation to disease state.

VNS can be modulated based on the physical activity measured by the accelerometer. For example, a decrease in physical activity can result in a modification of one or more stimulations parameters, such as more frequent stimulations (e.g. from once a day stimulation to twice a day stimulation), higher intensity/amplitude stimulations, and/or longer duration stimulations. In some embodiments, these adjusted stimulation parameters may be temporary or last for a predetermined duration, such as for up to 1, 2, 3, 4, 5, 6, 7, 14, 21, 30, 60, or 90 days, after which the system reverts back to the default stimulation parameters in order to avoid habituation. If the physical activity decreases again as a result of the reversion back to default stimulation parameters, the stimulation parameters can be adjusted as described above, and the default stimulation parameters may be updated to the adjusted parameters.

In some embodiments, a sensor can be used to measure heart rate (HR) and heart rate variability (HRV). As mentioned above, the HR/HRV sensor(s) may be integrated into the implant and/or separate from the implant. For example, an accelerometer worn on the torso over the heart may be able to detect the beating of the heart. In some embodiments, the accelerometer within the microstimulator can be used to detect the heart beat. Alternatively, the electrodes of the microstimulator and/or POD can be used to detect and measure electrical activity from the heart in order to measure heart rate and heart rate variability. For example, the stimulating electrodes of the microstimulator, when not delivering a stimulation, can be used to detect and measure electrical activity, such as an electrocardiogram do determine heart rate and HRV. In some embodiments, the heart rate data can be averaged over a period of time, such as hourly or daily, to generate a physical activity score, or help form the physical activity score along with the accelerometer data. In some embodiments, heart rate variability can be used to modulate stimulation parameters. In some embodiments, the heart rate variability can be correlated with physical activity or directly with the level of inflammation, or more generally, with the disease state. In some embodiments, both the heart rate variability and physical activity are inversely correlated with the level of inflammation. In other words, high levels of inflammation may be correlated with low levels of physical activity and low levels of heart rate variability. As described above for modulation of stimulation parameters based on physical activity, heart rate and/or heart rate variability can similarly be used to modulate stimulation parameters. For example, a decrease in average heart rate and/or a decrease in heart rate variability can result in a modification of one or more stimulations parameters, such as more frequent stimulations (e.g. from once a day stimulation to twice a day stimulation), higher intensity/amplitude stimulations, and/or longer duration stimulations.

Figure 10:
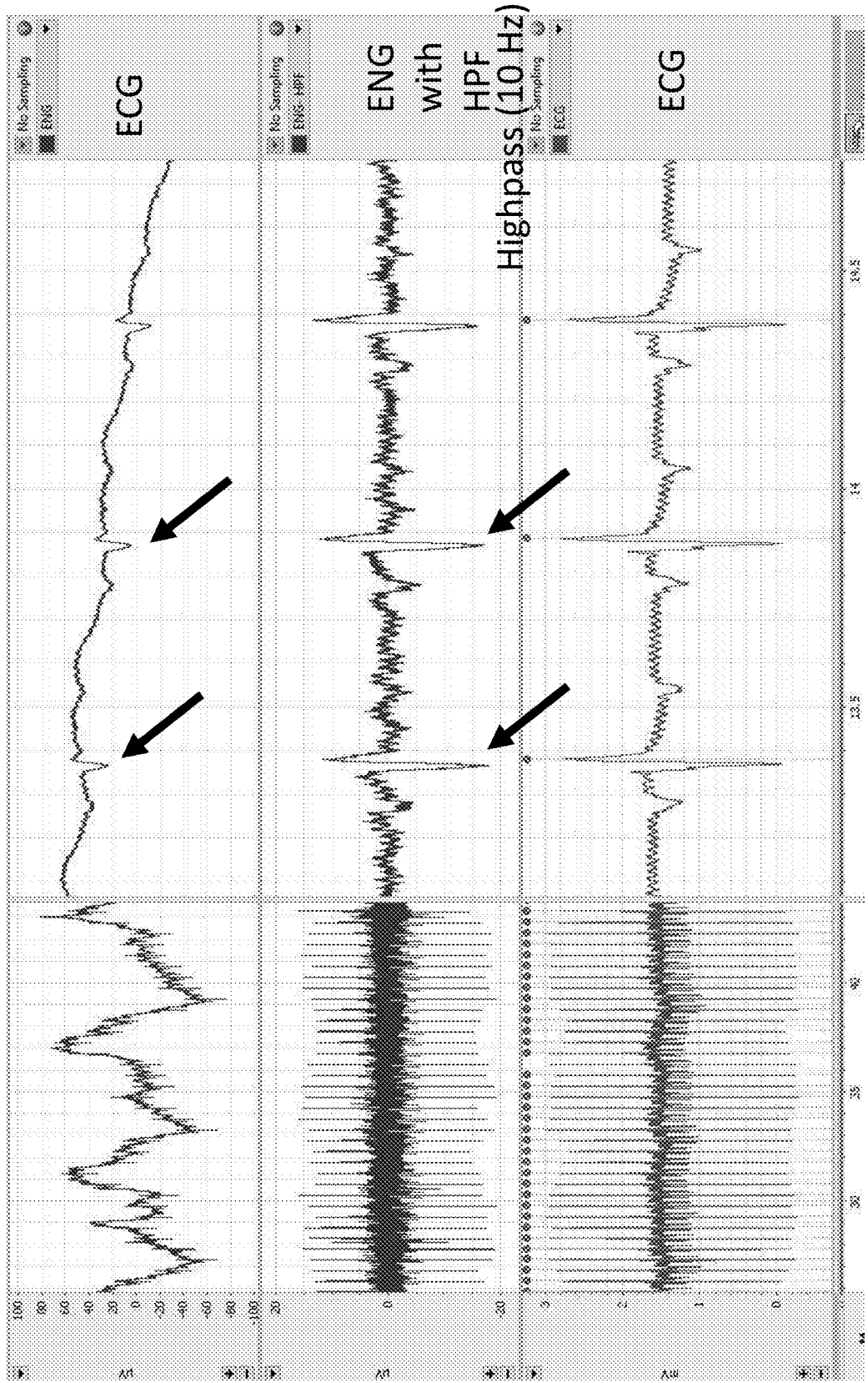
FIG. 10 illustrates an example of of the measure of heart rate (and therefore HRV) from an animal (dog) implanted with a microstimulator within a nerve cuff applied over a cervical region of the vagus nerve. An ECG signal, including R-peak information, may be isolated from the leads in contact with the vagus nerve within the cuff (shown in middle trace).
Figure 11:
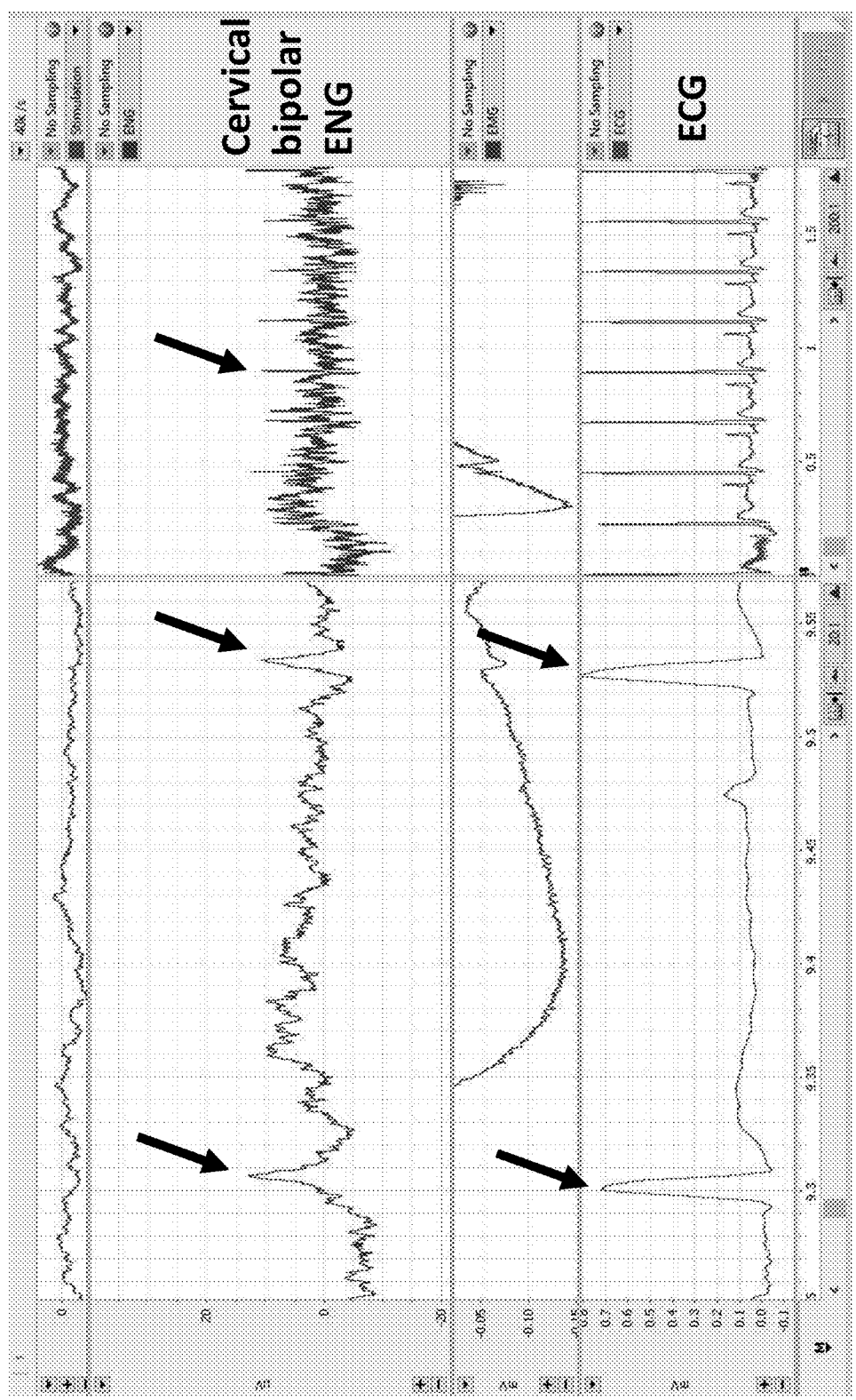
FIG. 11 is another example of the measurement of HR (and/or HRV) from an implanted microstimulator held within a nerve cuff on a cervical region of the vagus nerve for a rat.
Figure 12:
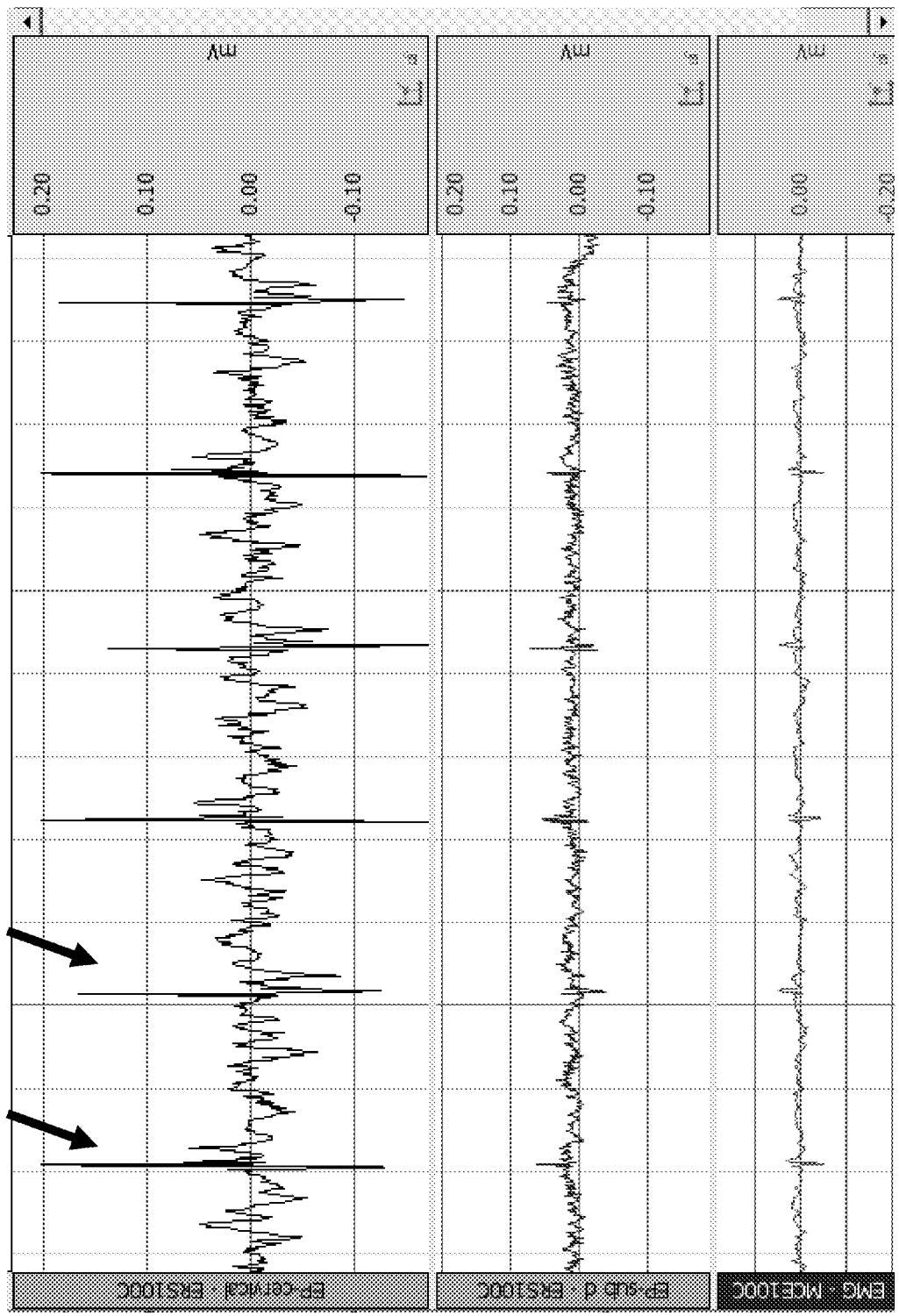
FIG. 12 shows another example of the measurement of HR (and/or HRV) from an implanted microstimulator held within a nerve cuff on a cervical region of the vagus nerve for a rat.

In some variations, it may be particularly beneficial to detect a parameter, such as heart rate and/or HRV, using the same electrodes that are used to apply the VNS. Although these electrodes are typically held in communication with the vagus nerve, the inventors have found a signal corresponding to ECG signal may be determined by measuring electrical activity across the bipolar electrodes within the cuff, as shown in FIGS. 10-12. In FIG. 10, for example, a cuff including a microstimulator was implanted on a canine cervical vagus, and an ECG signal was surprisingly found to be distinguishable from the bipolar electrodes on the cervical vagus with proper filtering. As shown in the middle trace, when a high-frequency filter (e.g., 10 Hz) was applied to the detected signal, an ECG signal was detected (compare to the measured ECG signal for the same animal, shown at the bottom trace). The scale in the middle trace is in microvolts, while the typical ECG signal is in millivolts. The top trace is unfiltered. The arrows show the peaks (R peaks) of the ECG waveforms.

A similar result was found for a cuff holding a bipolar cuff electrode (microstimulator) in a rat, as shown in FIG. 11, without filtering; FIG. 12 shows detection of the R-peak of the ECG of a rat within a bipolar cuff on the cervical vagus nerve of the rat.

Figure 13:
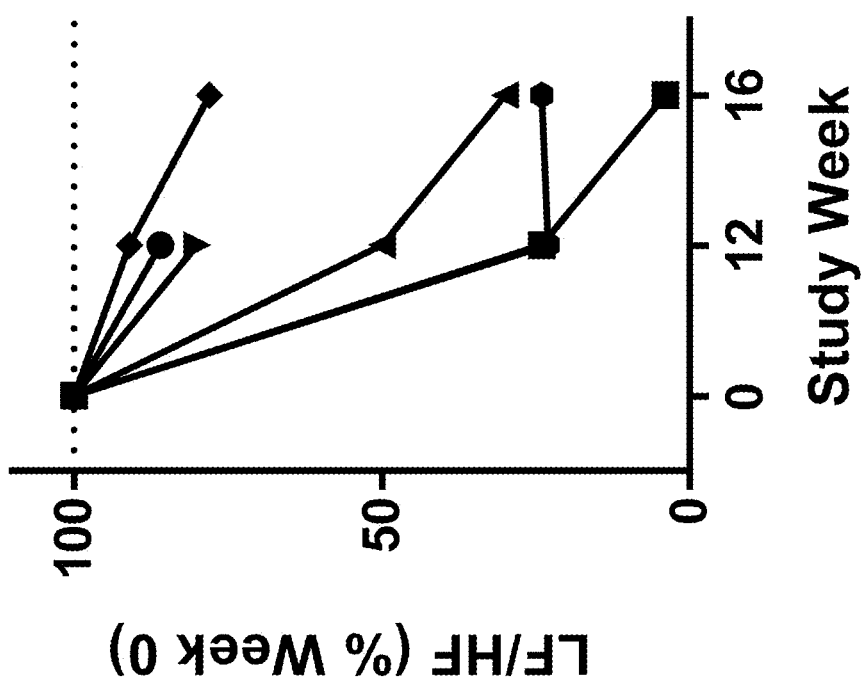
FIG. 13 illustrates the use of HRV to estimate treatment efficacy for VNS as described herein.

In general, heart rate variability (HRV) may provide an indicator of therapy efficacy, as it may effect vagal tone. For example, HRV may change as therapy is applied, as shown in FIG. 13, showing changes in HRV measured in a Crohn's patient over a treatment (study) period, comparing changes in the ratio of LF/HF from baseline (e.g., week 0) over time, where LF refers to the low-frequency power and HF is a measure of the high-frequency power. LF/HF ratio may be considered an indicator of the autonomic balance for the patient.

In some embodiments, HR and/or HRV can be determined before stimulation, during stimulation, and after stimulation. This allows the system and device to determine how the stimulation is affecting heart rate and/or HRV, and can also function as a safety mechanism. For example, in some embodiments, stimulation can be delayed or cancelled or aborted while in progress when the HR and/or HRV is above or below a predetermined threshold. In some embodiments, the predetermined thresholds can be determined based on a patient's normal resting HR and HRV, or a patient's sleeping HR and HRV if stimulation is applied when the patient is asleep. For example, the predetermined threshold can be about +/−10%, 20%, 30%, 40%, or 50% of the resting or sleeping HR and HRV. In some embodiments, the device and system can determine whether the stimulation is adversely affecting the patient's HR and/or HRV by comparing the HR and/or HRV from before, during, and after stimulation. If the stimulation is adversely affecting the HR and/or HRV, stimulation parameters can be adjusted, such as decreasing amplitude and/or duration and/or frequency of dosages, and/or the position of the implant on the vagus nerve can be adjusted.

In some embodiments, the microstimulator can be programmed to utilize the measured sensor data directly to modulate the stimulation parameters in a closed-loop implementation, as described above. In other embodiments, the sensor data, along with patient data including the status of the disease, such as inflammation, and the stimulation parameters and protocol, can be sent to the database stored on a computing device. The database and computing device can be server and/or part of a cloud computing network. For example, the data can be stored temporarily on the microstimulator, and can be periodically uploaded to the charger and/or prescription pad, and then transmitted to the external database. The external database can store data from a large population of patients using the same neurostimulation device to treat the same disease. From this collection of data, the server can compare the patient's stimulation parameters and protocol with patients sharing the same or similar characteristics, such as the same implant, the same disease (e.g., rheumatoid arthritis), and a similar response to VNS. The stimulation parameters can then be adjusted to match or be based on the stimulation parameters that were found to be successful in the similar group of patients. The server can then transmit these updated stimulation parameters to the microstimulator via the charger/prescription pad. In some embodiments, adjusting the stimulation parameters using the server with the external database can be combined with the closed-loop control of the microstimulator. For example, the server can be queried on a periodic basis, such as weekly, monthly, or quarterly, or on demand, to update the stimulation parameters, while the closed-loop control can remain active on an ongoing basis. In some embodiments, the data can be transmitted to a local computing device, such as the prescription pad, which can determine the modulation of the stimulation parameters. In some embodiments, the local computer may have a model database of patient parameters, disease state, and patient info that can be used to adjust the stimulation parameters. The model database can be updated on a regular basis, such as annually, semi-annually, or quarterly, for example.

User Interface for Implanted Neurostimulator

Also described herein are systems, including user interfaces for such systems, for user interaction with an implanted neurostimulator. The control software (including user interfaces) described herein may be used as part of any VNS apparatus, including, but not limited to, those described herein. In particular, described herein are apparatuses including a user interface for dynamic control of dose delivery of an implanted VNS microstimulator, such as those described herein. The dynamic control may provide an alert prior to delivery of a dose from an implanted microstimulator, and may present the user with a large, easy to read countdown of the time before the next dose, and permit the user to delay/postpone or cancel the scheduled dose. The user interface may illustrate in a timeline-like manner (showing night/day, hours, etc.) a graphic illustrating scheduled doses, and may allow the user to select a scheduled dose for delay or cancellation. In particular, the user interface may allow a user to select (using a control such as a slider, button, knob, etc.) a time period for delaying a dose within a predetermined time range (e.g., between 0.1 to 10 hour, etc.).

Any of the methods and user interfaces described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user/patient, analyzing, modifying stimulation parameters (including timing, frequency, intensity, etc.), determining, alerting, or the like.

The user interface may also present the user with a display during the delivery of a dose, and may include a large control (e.g., button, virtual button, switch, etc.) to stop or abort a delivered dose. The button may be between 10 and 50% the display size, and may be configured to attract the user's attention (by flashing, bright color, etc.).

Thus, described herein are systems, including user interfaces for such systems, for user interaction with an implanted neurostimulator. The implanted neurostimulator may in particular be a vagus nerve stimulation (VNS) apparatus as incorporated herein by reference.

In any of these systems, the system may be software, firmware and/or hardware including a user interface for displaying and allowing user interactivity, where the user is the patient into which the neurostimulator has been implanted. The system may confirm that the user has an implanted neurostimulator, and may include safety and/or encryption to prevent improper modification of implant parameters and/or receipt of implant data. Proximity detection (e.g., detecting a specific implant that has been paired with the system) may be used, e.g., by receiving wireless information (Bluetooth, etc.) from the implant. The system may communicate directly or indirectly with the implant, including through a charger or control system.

Figure 14:
FIG. 14 shows an overview of one variation of control software for a remote processor (e.g., smartphone) acting as a prescription pad, that may be used to regulate the application of dosing for an apparatus as described herein. The control software may provide an interface for operating the implant, including providing immediate feedback for the user in adjusting or delaying the dosing time and/or stopping or postponing a dose. The control software may also encourage patients to conduct best practices for their treatment.

FIG. 14 shows an example of user interface for a handheld control device (e.g., smartphone) that communicates with an implanted microstimulator, either directly or indirectly (e.g., through a charger/control loop). In FIGS. 14-25, the control logic (user interface) is configured to operate on a handheld device such as a pad, tablet or smartphone. In FIG. 14, the system includes a series of user interface "screens" for displaying the dose being delivered (and allowing the user to halt/stop dose delivery), the time to the next dose and scheduling controls, including delaying, postponing or cancelling a dose, and user dosage history, including in particular gamification of the user dosage history, by including virtual awards, badges or the like.

Figure 15:
FIG. 15 illustrates an example of a control screen to be displayed to a user when the apparatus is delivering a dose ("dose in process") and may provide a simple and large control interface (e.g., virtual button) for stopping the dose, as well as a countdown timer showing the duration of the dose in progress.

FIG. 15 illustrates the user interface showing a display of a dose in progress, including a timer (e.g., count-down or count-up clock) 1501 and a button to start/stop the dose 1503. The user interface may also include navigation controls to display scheduled doses, achievements (user history) and settings. This screen can change to provide immediate access to stop dose delivery.

Figure 16:
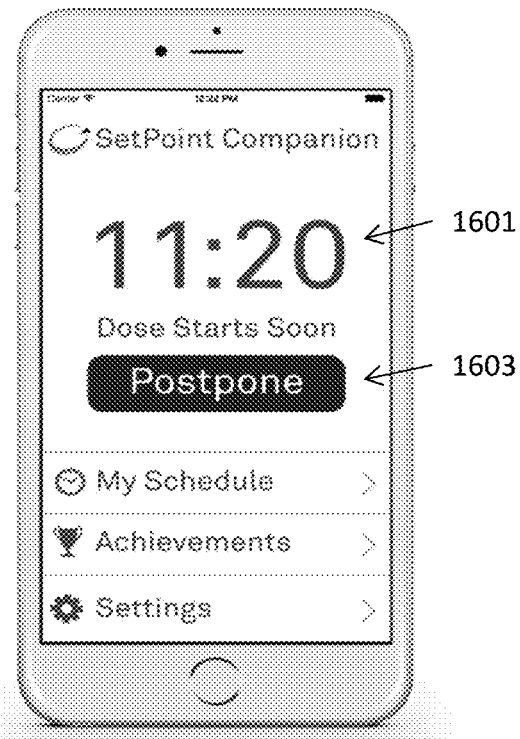
FIG. 16 shows an example of a control screen showing a countdown until the delivery of the next scheduled dose, and providing a simple and large control (e.g., virtual button) for postponing delivery of a dose.

FIG. 16 is an example of a user interface screen displaying a time to next dose delivery counter 1601 and a control (shown as button 1603) to allow a user to postpone or delay (or in some variations, cancel) a scheduled dose. The user interface screen shown in FIG. 16 can change to provide immediate access to postpone dose when between reminder and dose. As mentioned, the user interface may alternatively or additionally include a dose canceller.

Figure 17A:
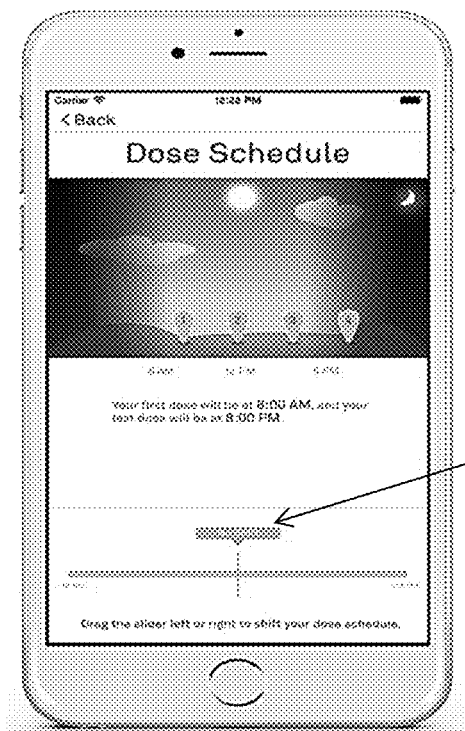
FIG. 17A illustrates a first example of a dose scheduling screen including a user control input (e.g., button, slider, dial, etc.) 1701 for shifting the time for delivery of the next dose by a selectable amount, which may be selectable within a predetermined range.

FIG. 17A is an example of a user interface that permits a user to dynamically delay or postpone the delivery of VNS from an implanted microstimulator on the vagus nerve in which the user may operate a control (shown as a virtual control, e.g., a slider, button, knob, etc.) to select the duration of the delay before delivering the next dose. In this example, the user slides her or his thumb (left or right) on either the slider control or the landscape to shift the schedule. The user may select which dose (doses are shown displayed/flagged on a graphical timeline showing day/night), and move the slider more or less to shift the time the dose is to be delivered (earlier or later than the scheduled time for a particular dose on a particular day). Each dose may be adjusted individually, or adjusting one dose may alter the timing of one or more adjacent doses. As shown in FIG. 17A, the display may show the day/night approximation of doses using graphics and/or color. In this example, the user has a full 24-hour range of control. Some patients may find it convenient delivery of a dose based on their activity or work schedule; for example if the patient switches a work shift from day shift to night shift. In some patients with an implantable VNS microstimulator, VNS may cause, as a side effect, a mild hoarseness or throat irritation, which may be less noticeable when asleep; thus, it may be beneficial to schedule dose delivery when such side effects may be less bothersome.

Figure 17B:
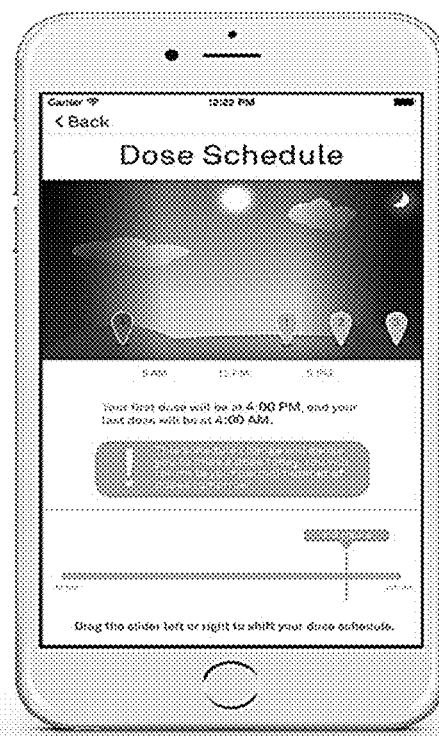
FIG. 17B is another example of a dose scheduling screen showing shifting of a dose time, including a warning indicating that the time-shifting of the dose may result in a dose being skipped.
Figure 18A:
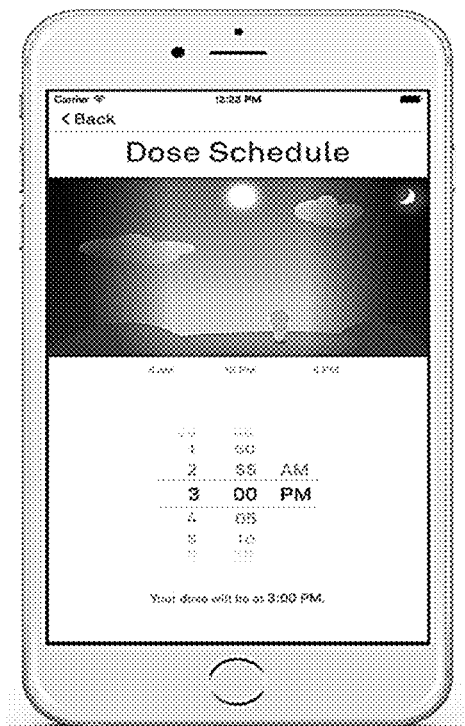
FIG. 18A illustrate an example of a dose scheduling screen that is configured to allow a user to manually schedule a VNS dose to be delivered by the implant.
Figure 18B:
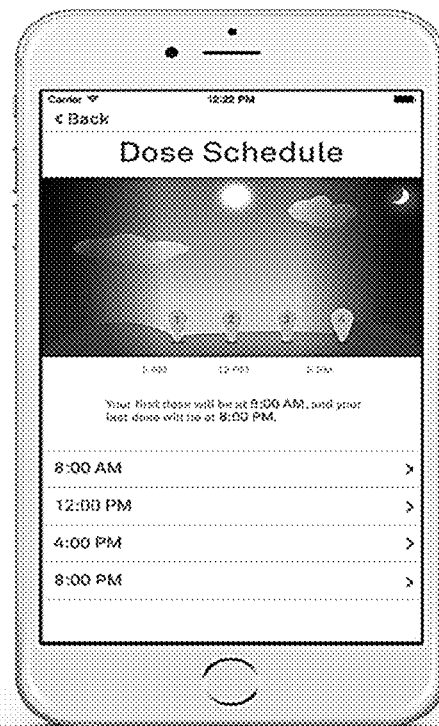
FIG. 18B is another example of a dose scheduling screen (user interface) that lists and graphically displays the doses to be delivered.

FIG. 17B illustrates the use of the dose scheduler, showing shifting of the dose 8 hours forward, as well as a warning that this may result in a dose being missed. FIGS. 18A and 18B illustrate dose scheduling using a user interface as described herein. Users with only one dose per day can have a simplified dose screen, similar to that shown in FIG. 18A, that simply schedules when their dose occurs. In FIG. 18A, this is a selectable timer picking the time of day and a graphic. In FIG. 18B, previous dose shift screens are predicated on clinician determining dose spacing; these four doses shown may be scheduled +/− some hours which the user may select. More explicit dose scheduling may occur depending on the preferences of the clinician. The user may therefore select a dose and adjust up/down the timing for this dose. Such adjustments may be done for every day or for particular days of the week.

Figure 19:
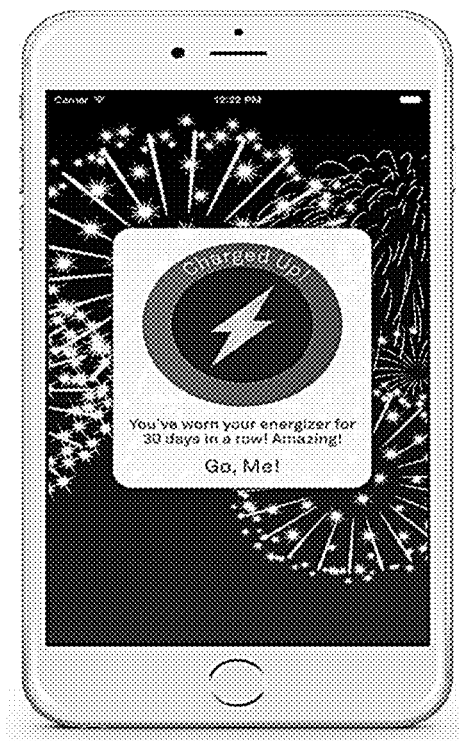
FIG. 19 illustrates one example of gamification of dose delivery, showing a congratulatory screen.
Figure 20:
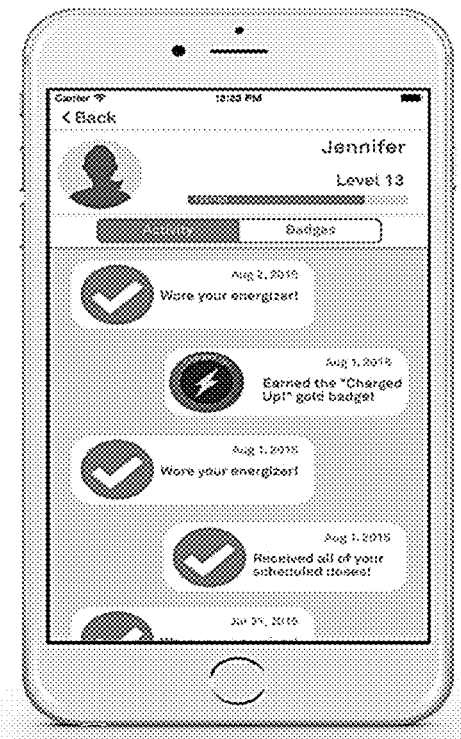
FIG. 20 is a user interface illustrating a list of achievements unlocked by the user in operating the system.
Figure 21:
FIG. 21 is an example of virtual awards or badges that may be rewarded to the user by the user interface to encourage compliance.
Figure 22:
FIG. 22 is an example of an alert that may be provided by the user interface.

Any of the user interfaces described herein may be configured to enhance and encourage user treatment (accepting dosage delivered) and compliance by 'gamification' of the dosing via the user interface. For example, FIG. 19 shows an example of a virtual award (e.g., badge, button, token, etc.) which may be kept virtual or may be exchanged or be a placeholder for an actual award, button, token, etc. Such awards may be provided to encourage user compliance and best practices. Similarly, FIGS. 20 and 21 illustrate achievements and "badges" that may be provided as part of the user interface or other user experience. In FIG. 20, the user may be awarded levels which may give users bragging rights and keep them interested in keeping up their good habits. "Achievements" may be stored and viewed to provide a historical view of good habits (and possibly bad) to the user as part of the user interface. FIG. 21 illustrate examples of user "badges" that may be awarded. Examples of such badges may include: charging MR/using Energizer; Not Skipping Doses; Using Energizer to sync when changing time zones; Encourage better overall health through exercise; Frequent app use; Exploring various parts of the app, etc.

In any of the apparatuses described herein, the apparatus (e.g., including control software/user interface) may provide notices/notifications prior to dose delivery. For example, in some variations the apparatus may transmit a reminder (interrupt, push notification, etc.) prior to delivery of a dose at a predetermined time (e.g., 1 minute, 5 minutes, 10 minutes, 15 minutes, 20 minutes, 30 minutes, 60 minutes, etc.), and/or may display a countdown, as illustrated above. Thus, the apparatus may offers reminders (without stimulation) when a dose is about to occur and/or permit rescheduling or cancelling of a dose. The apparatus may provide an alert for other conditions (e.g., need to charge MR or energizer, need to time sync because of time zone change, etc.) in addition or instead of pre-dose alerts.

Figure 23:
FIG. 23 is an example of a user interface indicating the timing of a scheduled dose; within a predetermined time before the delivery of the next dose, the apparatus/user interface may automatically present the user with a warning/countdown screen indicating the time before the next dose, and presenting a button/control to defer/delay or cancel this dose.
Figure 24:
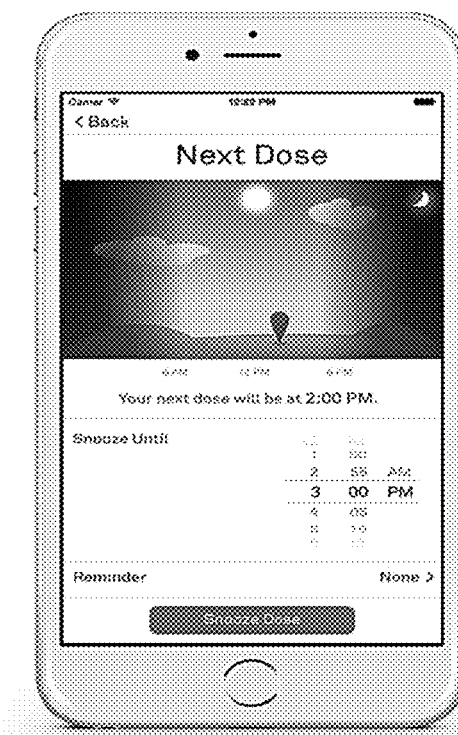
FIG. 24 illustrates a next dose screen, illustrating the date of the next scheduled dose, and also illustrates a "snooze" control that may be part of the user interface, permitting the user to select the time increment for deferring the dose delivery.

In any of the variations described herein, the apparatus may provide for editing (e.g., 'next dose editing') of any of the scheduled doses, as illustrated in FIG. 23, showing a "Next Dose" selection to present the user with the next dose screen shown in FIG. 24. In this example, the "Next Dose" screen allows direct editing of the next dose time, as well as whether there will be a reminder. In this example, tapping on a home screen reminder would bring you directly to this screen.

Figure 25:
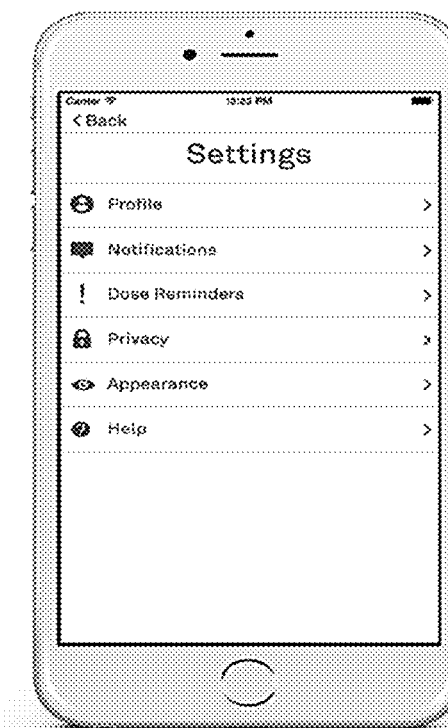
FIG. 25 illustrates exemplary settings for a user interface as described herein.

FIG. 25 illustrates an example of settings that may be modified in any of the user interfaces described herein. for example, the user may input or select the profile (e.g., Name, Avatar, and other demographic info, etc.), modifying notifications (e.g., what alerts the application is permitted to present); dose reminders (e.g., change the timespan between the reminder dose and actual dose stimulation); privacy (e.g., input or require a PIN or TouchID settings for App, Opt-In/Out for sharing data with SPM), appearance (e.g., display and content options for app, accessibility, etc.); and help (e.g., information and access to patient support).

Figure 26:
FIG. 26 illustrates a variation of the user interface (similar to that shown in FIGS. 14-25, above, configured to operate on or as part of a wearable apparatus (e.g., smartwatch).
Figure 27:
FIG. 27 illustrates a control screen including a stop/cancel button for deferring or delaying delivery of a dose, configured to operate on a wearable smartwatch apparatus.
Figure 28:
FIG. 28 illustrates a user interface for a wearable apparatus (smartwatch) displaying virtual awards or badges that may be rewarded to the user by the user interface to encourage compliance.

Although the examples shown above are shown as configured to use on a smartphone, or pad, they may alternatively or additionally be configured to operate on a wearable electronic device, such as a watch (e.g., smartwatch, etc.), as shown in FIGS. 26-28.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for treating inflammation, the system comprising:
   an implantable microstimulator configured to apply neural stimulation to a cholinergic anti-inflammatory pathway (NCAP);
   an external programmer configured to communicate with the implantable microstimulator; and
   a non-transitory computer-readable medium including computer-program instructions, that, when executed by one or more processors, perform a computer-implemented method comprising:
      presenting a user interface for adjusting stimulation parameters of the implantable microstimulator;
      receiving user input for adjusting or delaying dosing delivered by the implantable microstimulator;
      confirming that the external programmer is paired with the implantable microstimulator before transmitting the user input; and
      transmitting the user input indirectly to the implantable microstimulator through the external programmer when the external programmer is paired with the implantable microstimulator.

2. The system of claim 1, wherein the implantable microstimulator is a leadless implantable microstimulator.

3. The system of claim 1, wherein the non-transitory computer-readable medium is configured to execute on a user's mobile device.

4. The system of claim 1, wherein the external programmer comprises a charger.

5. The system of claim 1, wherein the computer-implemented method further comprises receiving data associated with a patient metric and adjusting the dosing based on the patient metric.

6. The system of claim 5, wherein the patient metric comprises a biomarker for inflammation.

7. The system of claim 6, wherein the biomarker for inflammation comprises a cytokine level and/or a memory T cell level.

8. The system of claim 5, wherein the patient metric comprises an activity metric or a physiological metric.

9. The system of claim 1, further comprising receiving, from the user interface, an emergency stop command and transmitting the emergency stop directly to the implantable microstimulator.

10. The system of claim 1, wherein receiving user input for adjusting or delaying dosing delivered by the implantable microstimulator comprises receiving the user input when the external programmer is not in communication with the implantable microstimulator.

11. The system of claim 1, wherein the external programmer is configured to prevent improper modification of dosing.

12. A system for treating inflammation, the system comprising:
    an implantable microstimulator configured to apply neural stimulation to a cholinergic anti-inflammatory pathway (NCAP);
    an external programmer configured to communicate with the implantable microstimulator; and
    a non-transitory computer-readable medium including computer-program instructions, that,
       when executed by one or more processors, perform a computer-implemented method comprising:
          presenting a user interface for adjusting stimulation parameters of the implantable microstimulator;
          receiving user input for adjusting or delaying dosing delivered by the implantable microstimulator;
          confirming that the external programmer is paired with the implantable microstimulator;
          transmitting the user input indirectly to the implantable microstimulator through the external programmer when the external programmer is paired with the implantable microstimulator; and
          receiving an emergency stop and directly transmitting the emergency stop to the implantable microstimulator.

13. A method of treating inflammation using an implantable microstimulator configured to apply neural stimulation to a cholinergic anti-inflammatory pathway (NCAP), an external programmer configured to communicate with the implantable microstimulator, and a user's mobile device, the method comprising:
    presenting a user interface for adjusting stimulation parameters of the implantable microstimulator on the user's mobile device;
    receiving, through the user interface, user input for delaying dosing by the implantable microstimulator or adjusting stimulation parameters of the implantable microstimulator for dosing delivered by the implantable microstimulator, wherein the user input for delaying dosing is received when the external programmer is not in communication with the implantable microstimulator;

confirming that the external programmer is paired with the implantable microstimulator;

transmitting the user input from the user's mobile device indirectly to the implantable microstimulator through the external programmer when the external programmer is paired with the implantable microstimulator; and adjusting the implantable microstimulator based on the user input.

14. The method of claim 13, wherein the implantable microstimulator is a leadless implantable microstimulator.

15. The method of claim 13, wherein the external programmer comprises an inductive charger.

16. The method of claim 13, further comprising receiving data associated with a patient metric and adjusting the dosing based on the patient metric.

17. The method of claim 16, wherein the patient metric comprises a biomarker for inflammation.

18. The method of claim 17, wherein the biomarker for inflammation comprises a cytokine level and/or a memory T cell level.

19. The method of claim 16, wherein the patient metric comprises an activity metric or a physiological metric.

20. The method of claim 13, further comprising receiving an emergency stop and transmitting the emergency stop directly to the implantable microstimulator.

21. The method of claim 13, further comprising preventing, by the external programmer, improper modification of dosing.

22. A system for treating inflammation, the system comprising:

an implantable microstimulator configured to apply neural stimulation to a cholinergic anti-inflammatory pathway (NCAP);

an external programmer configured to communicate with the implantable microstimulator; and a non-transitory computer-readable medium including computer-program instructions, that, when executed by one or more processors, perform a computer-implemented method comprising:

presenting a user interface for adjusting stimulation parameters of the implantable microstimulator;

receiving user input for adjusting or delaying dosing delivered by the implantable microstimulator, wherein the user input for adjusting or delaying dosing is received when the external programmer is not in communication with the implantable microstimulator;

confirming that the external programmer is paired with the implantable microstimulator; and transmitting the user input indirectly to the implantable microstimulator through the external programmer when the external programmer is paired with the implantable microstimulator.

23. A system for treating inflammation, the system comprising:

an implantable microstimulator configured to apply neural stimulation to a cholinergic anti-inflammatory pathway (NCAP);

an external programmer configured to communicate with the implantable microstimulator, wherein the external programmer is configured to prevent improper modification of dosing; and a non-transitory computer-readable medium including computer-program instructions, that, when executed by one or more processors, perform a computer-implemented method comprising:

presenting a user interface for adjusting stimulation parameters of the implantable microstimulator;

receiving user input for adjusting or delaying dosing delivered by the implantable microstimulator;

confirming that the external programmer is paired with the implantable microstimulator; and transmitting the user input indirectly to the implantable microstimulator through the external programmer when the external programmer is paired with the implantable microstimulator.

\* \* \* \* \*